US008148119B2

(12) United States Patent
Fujii et al.

(10) Patent No.: US 8,148,119 B2
(45) Date of Patent: Apr. 3, 2012

(54) HYDROXYLASE GENE AND USE THEREOF

(75) Inventors: Yoshikazu Fujii, Iwata (JP); Tomohiro Tamura, Sapporo (JP)

(73) Assignees: Microbiopharm Japan Co., Ltd., Tokyo (JP); National Institute of Advanced Industrial Science and Technology, Tokyo (JP)

( * ) Notice: Subject to any disclaimer, the term of this patent is extended or adjusted under 35 U.S.C. 154(b) by 547 days.

(21) Appl. No.: 12/302,876

(22) PCT Filed: May 18, 2007

(86) PCT No.: PCT/JP2007/060254
§ 371 (c)(1),
(2), (4) Date: Nov. 28, 2008

(87) PCT Pub. No.: WO2007/138894
PCT Pub. Date: Dec. 6, 2007

(65) Prior Publication Data
US 2010/0297712 A1    Nov. 25, 2010

(30) Foreign Application Priority Data
May 31, 2006    (JP) ................................. 2006-150843

(51) Int. Cl.
*C12P 15/00*    (2006.01)
*C12N 1/20*    (2006.01)
*C07H 21/04*    (2006.01)

(52) U.S. Cl. .................. 435/127; 435/252.1; 435/320.1; 435/195; 536/23.2

(58) Field of Classification Search .................. 435/183, 435/127, 252.3, 320.1, 195; 536/23.2
See application file for complete search history.

(56) References Cited

U.S. PATENT DOCUMENTS
4,892,821 A    1/1990    Omura et al.

FOREIGN PATENT DOCUMENTS
JP    02231089 A    9/1990
JP    04064678 B2    10/1992

OTHER PUBLICATIONS

Sequence alignment between accession No. AAZ56003 and SEQ ID No. 1.*
English translation of International Preliminary Report dated Dec. 24, 2008, issued in International Application No. PCT/JP2007/060254.
International Search Report dated Jul. 17, 2007 corresponding to JP 2007/060254.
Sawada et al., Conversion of viatmin $D_3$ to $1_\alpha,25$-dihydroxyvitamin $D_3$ by *Streptomyces griseolus* cytochrome P450SU-1, Biochemical and Biophysical Research Communications No. 320, (2004) pp. 156-164.
Sasaki et al., Transformation of vitamin $D_3$ to $1_\alpha 25$-dihydroxyvitamin $D_3$ via 25-hydroxyvitamin $D_3$ using *Amycolata* sp. strains, Applied Microbiology Biotechnology (1992) vol. 38 No. 2: pp. 152-157.
Takeda et al., Application of Cyclodextrin to Microbial Transformation of Vitamin $D_3$ to 25-Hydroxyvitamin $D_3$ and $1_\alpha 25$-Dihydroxyvitamin $D_3$, Journal of Fermentation and Bioengineering, vol. 78, No. 5, pp. 380-382. 1994.
Kawauchi et al., Cloning and nucleotide sequence of a bacterial cytochrome P-450$_{VD25}$ gene encoding vitamin D-3 25 hydroxylase, Biochimica et Biophysica Acta, 1219, (1994) pp. 179-183.
O'Keefe et al., Identification of constitutive and herbicide inducible cytochromes P-450 in *Streptomyces griseolus*, Archives of Microbiology, (1998), 149, pp. 406-412.
Sakaki et al., Metabolism of Vitamin $D_3$ by Cytochromes P450, Frontiers in Bioscience, 10, pp. 119-134 (2005).
Supplementary European Search Report dated Oct. 8, 2009 in corresponding European Patent Application No. 07 74 3689.7.
H. Kawauchi, et al., "Cloning and nucleotide sequence of a bacterial cytochrome $P-450_{VD25}$ gene encoding vitamin D-3 and 25-hydroxylase," Biochimica et Biophysica Acta, Sep. 13, 1994, pp. 179-183, vol. 1219, No. 1, Elsevier Science B.V.
S. G. Hong, et al., Database WPI Week 200411, Thomson Scientific, London, Great Britain, Sep. 26, 2003, p. 1.
I. Nagy, et al., "Degradation of the Thiocarbamate Herbicide EPTC (S-Ethyl Dipropylcarbamothioate) and Biosafening by *Rhodococcus* sp. Strain NI86/21 involve an Inducible Cytochrome P-450 System and Aldehyde Dehydrogenase," Journal of Bacteriology, Feb. 1995, pp. 676-687, vol. 177, No. 3, American Society for Microbiology.
S. Warwick, et al., "A Phylogenetic Analysis of the Family *Pseudonocardiaceae* and the Genera *Actinokineospora* and *Saccharothrix* with 16S rRNA Sequences and a Proposal to Combine the Genera *Amycolata* and *Pseudonocardia* in an Emended Genus *Pseudonocardia*," International Journal of Systematic Bacteriology, Apr. 1994, pp. 293-299, vol. 44, No. 2, International Union of Microbiological Societies.
Y. Yoshikazu, et al., "Purification, characterization, and directed evolution study of a vitamin $D_3$ hydroxylase from *Pseudonocardia autotrophica*," Biochemical and Biophysical Research Communications, Jul. 24, 2009, pp. 170-175, vol. 385, No. 2, Elsevier Inc.

* cited by examiner

*Primary Examiner* — Tekchand Saidha
(74) *Attorney, Agent, or Firm* — Sughrue Mion, PLLC

(57) ABSTRACT

A vitamin $D_3$ hydroxylase is purified from *Pseudonocardia autotrophica* cell, and a primer is designed based on amino acid sequence obtained from hydroxylase. Subsequently, PCR is conducted using genomic DNA of *Pseudonocardia autotrophica* as a template to clone a gene for the vitamin $D_3$ hydroxylase. By conducting a conversion reaction using a microorganism in which the vitamin $D_3$ hydroxylase gene is expressed using a proper expression system, a hydroxide of vitamin D or the like (e.g., hydroxy vitamin $D_3$) can be produced with high efficiency.

9 Claims, 10 Drawing Sheets

[Fig. 1]
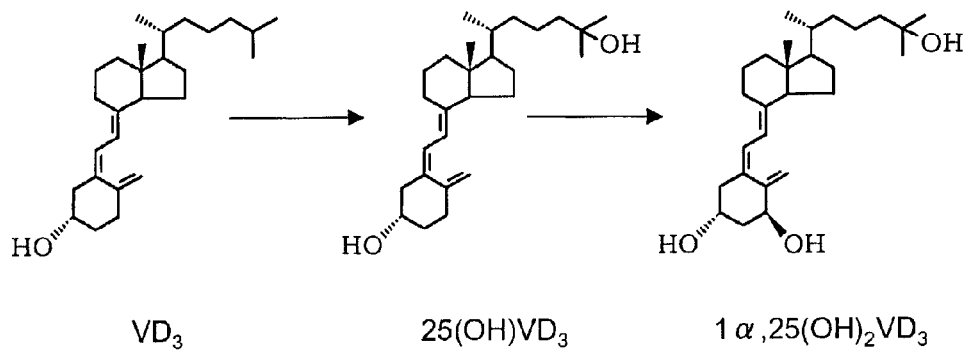
VD₃ → 25(OH)VD₃ → 1α,25(OH)₂VD₃
[Fig. 2]
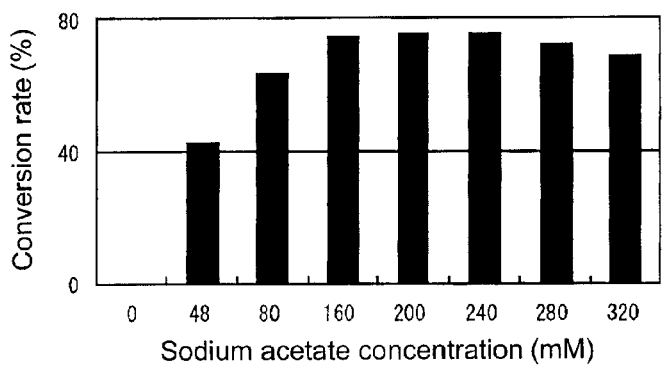
[Fig. 3]
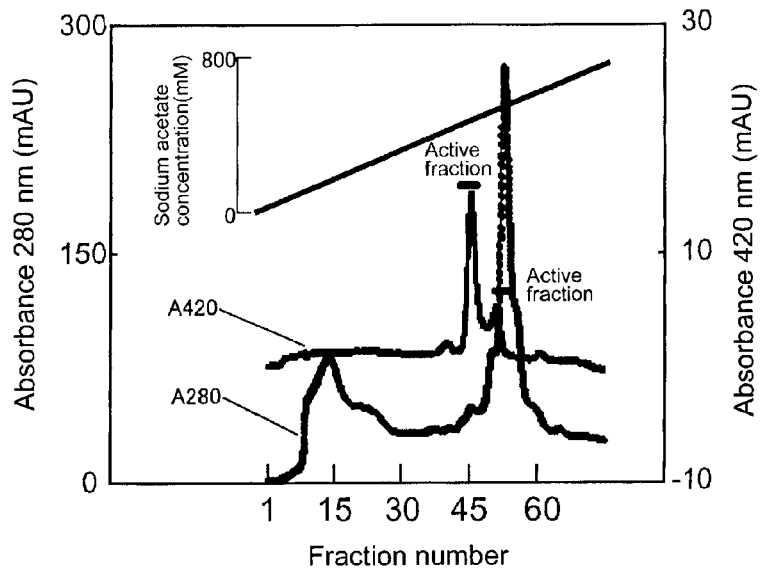

[Fig. 4]
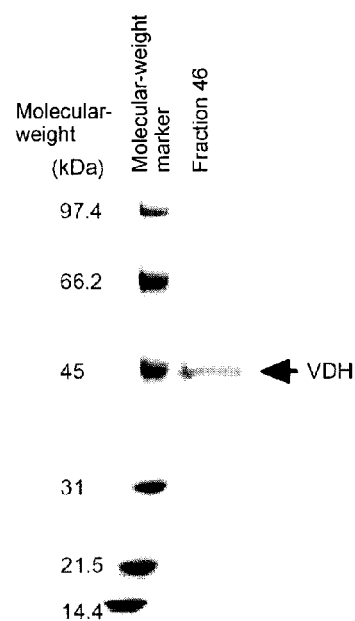
[Fig. 5]
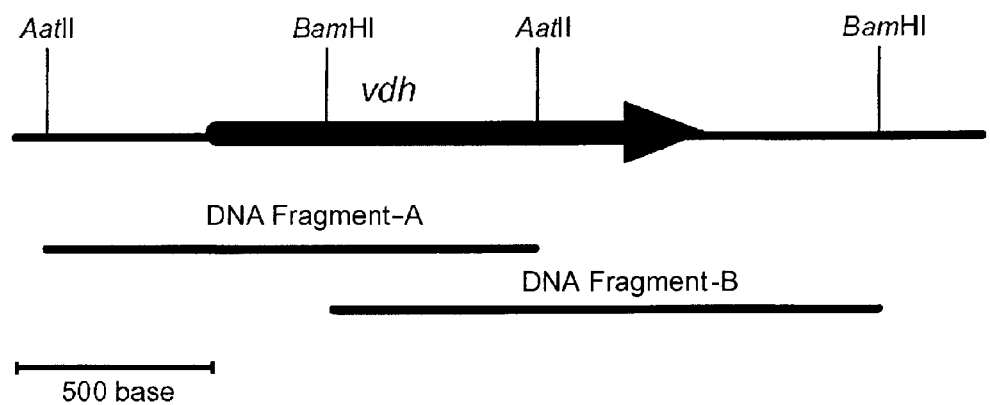

[Fig. 6]
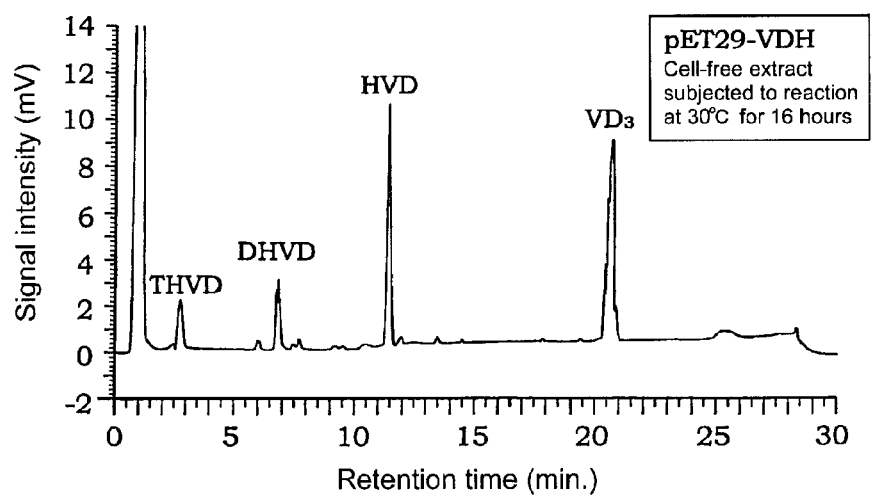
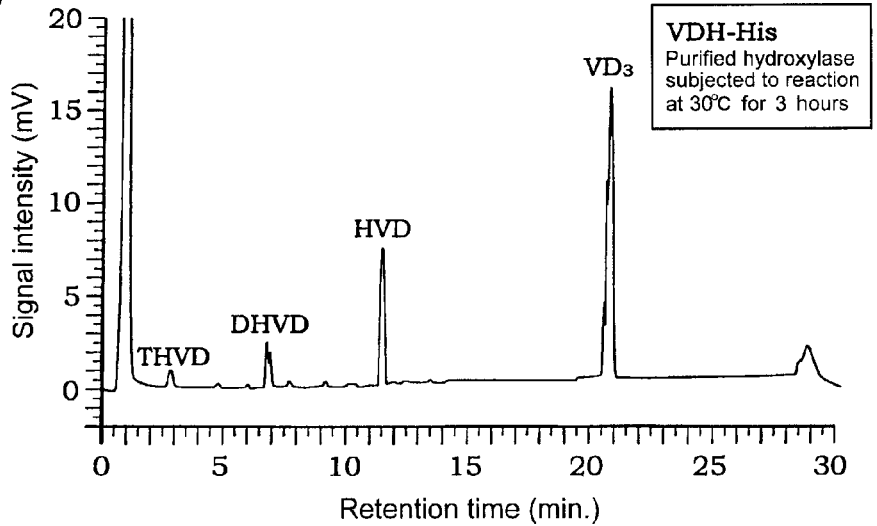

[Fig. 7]
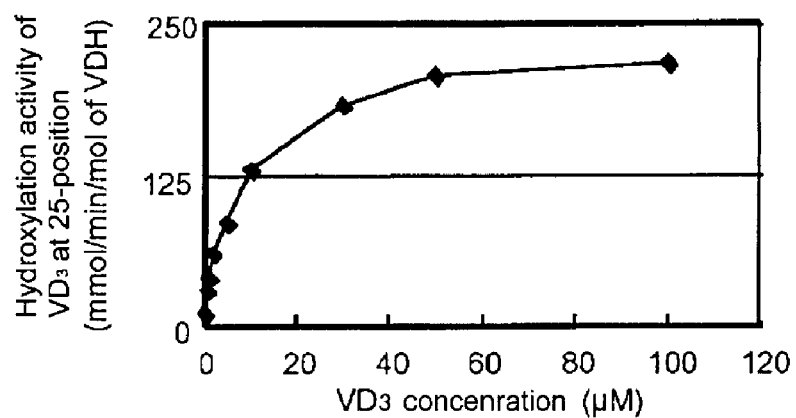
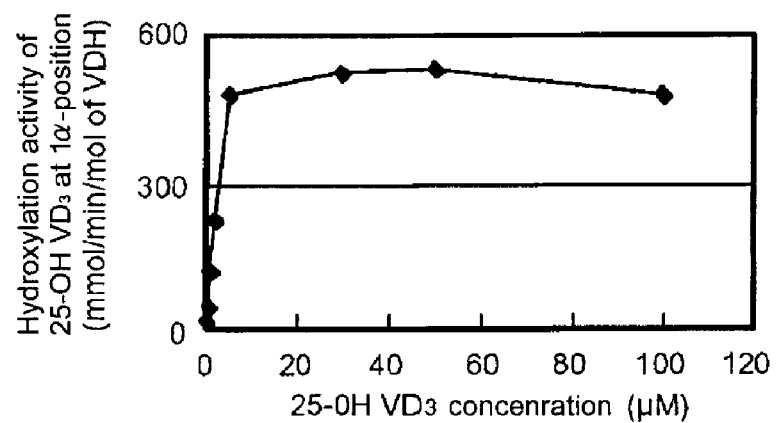

[Fig. 8]
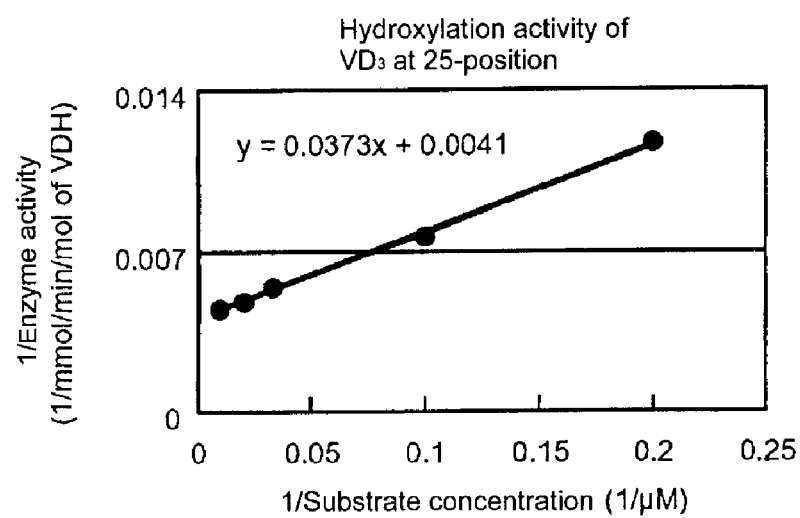
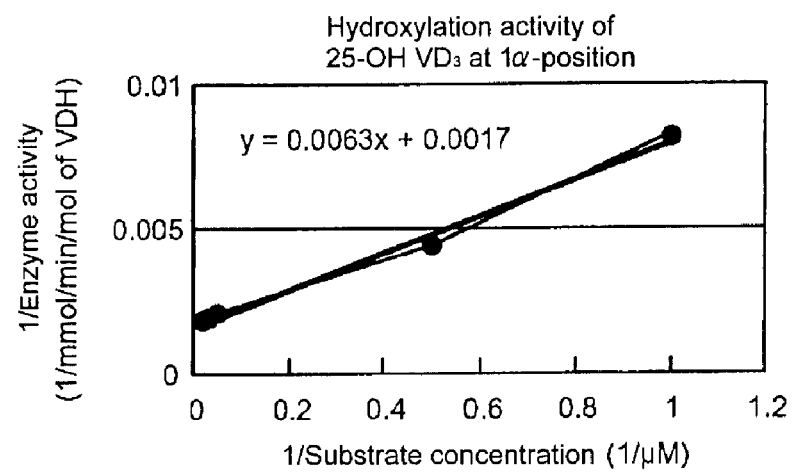

[Fig. 9]
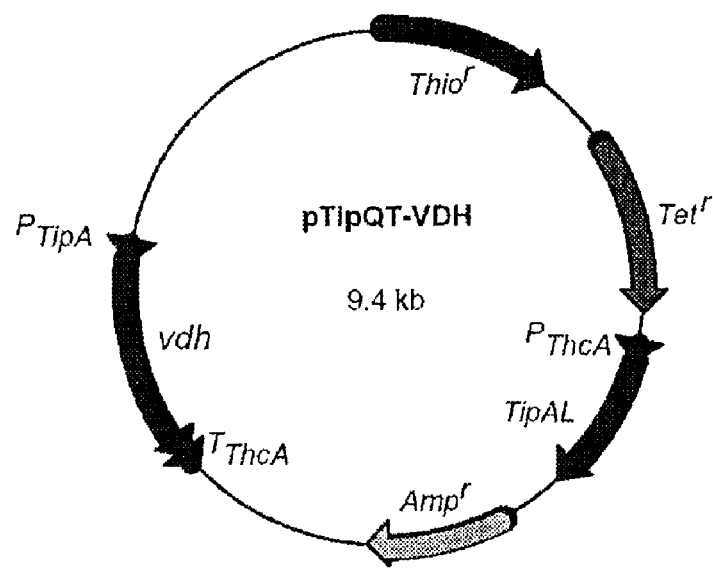
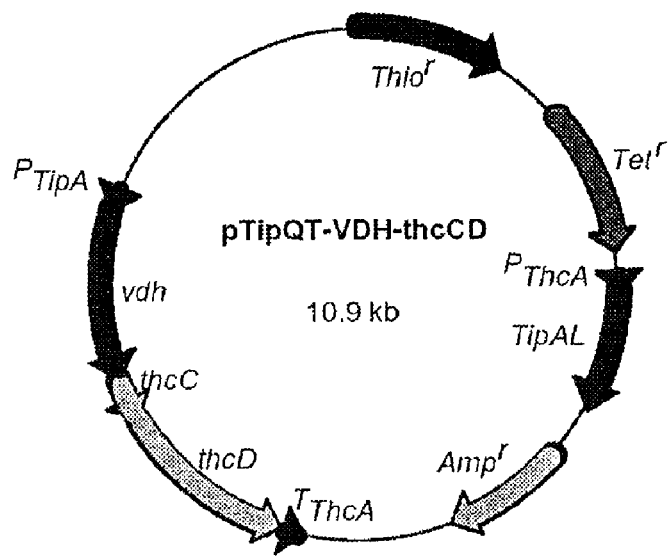

[Fig. 10]
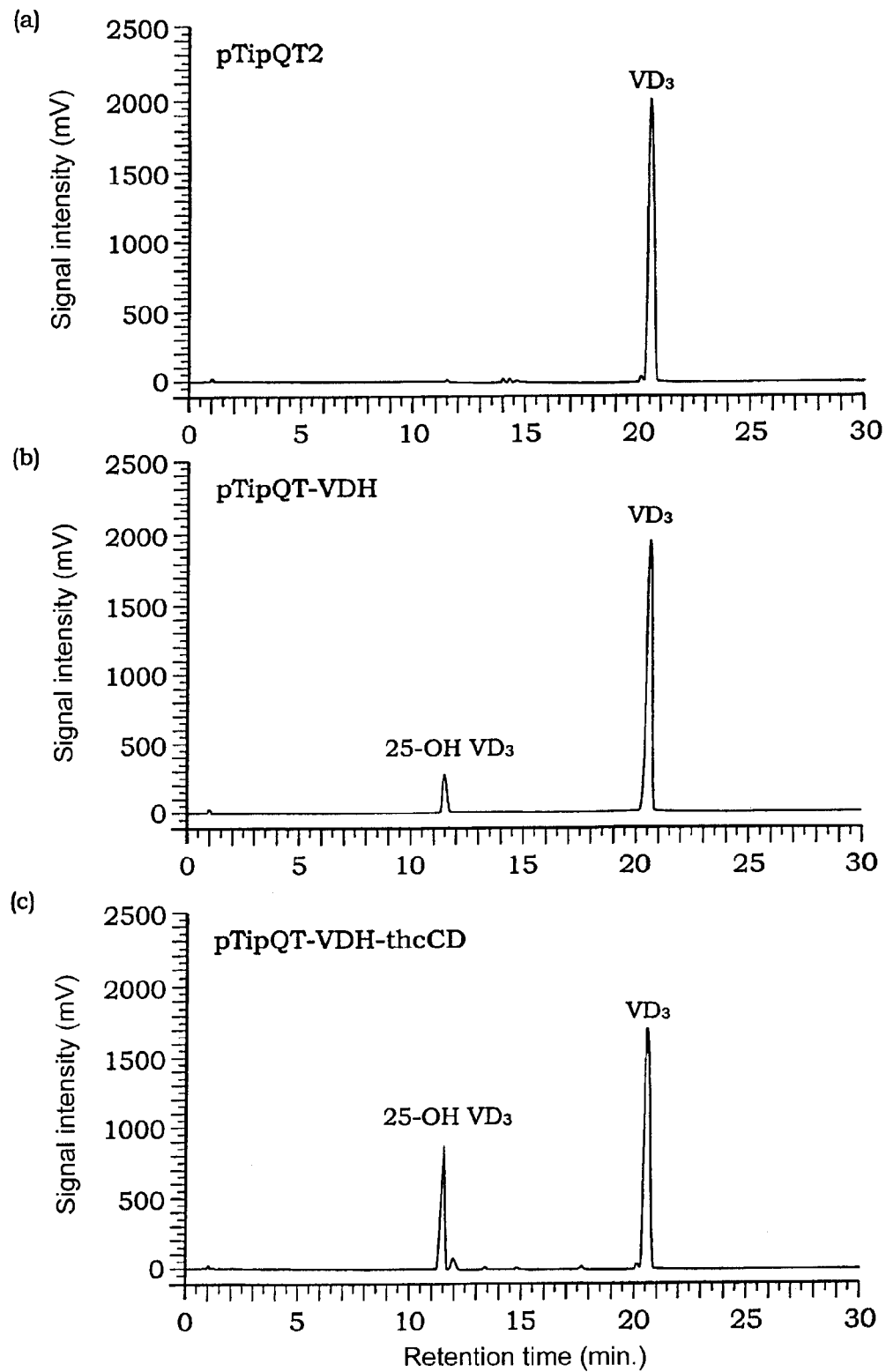

[Fig. 11]
(a)
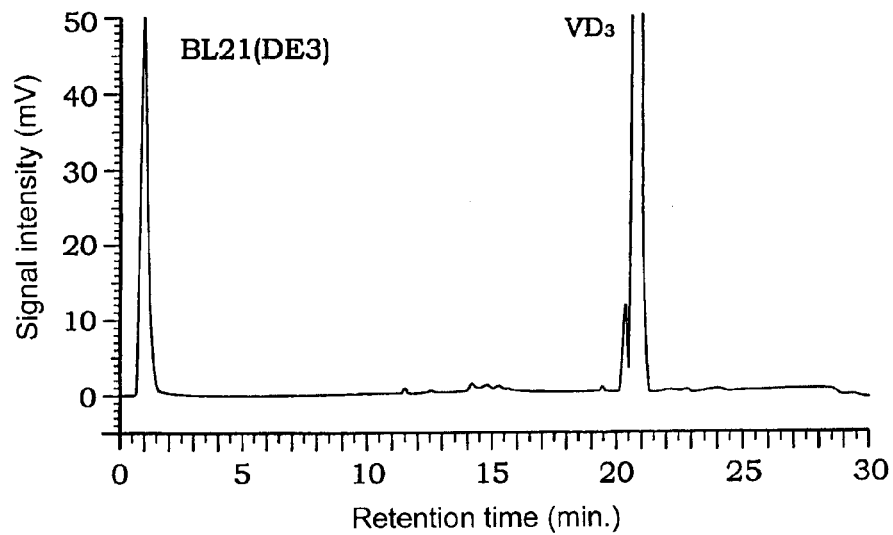
(b)
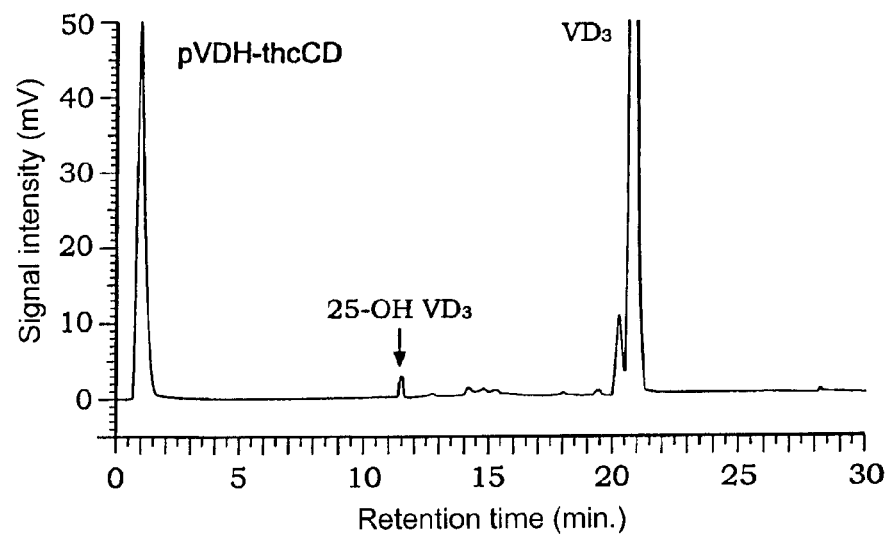

[Fig. 12]
Conversion test of VD₂
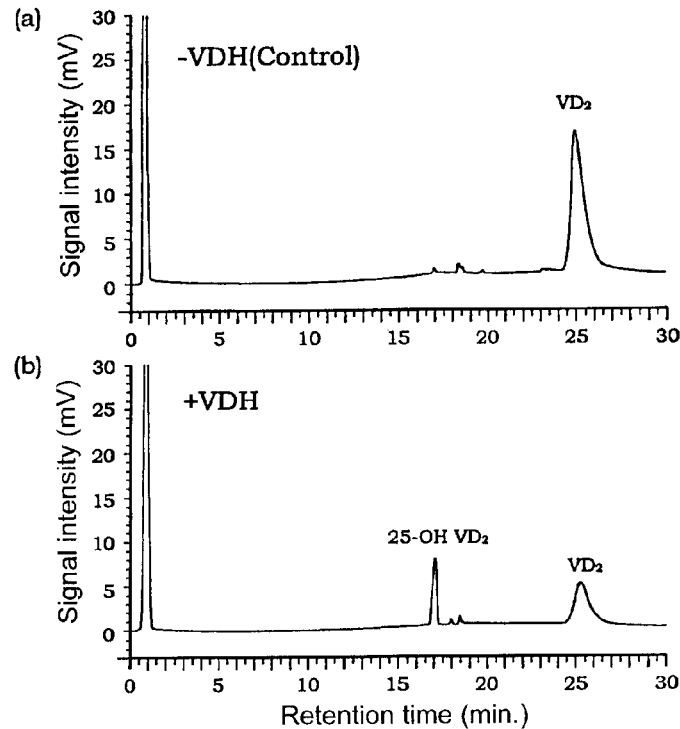
Conversion test of 25-OH VD₂
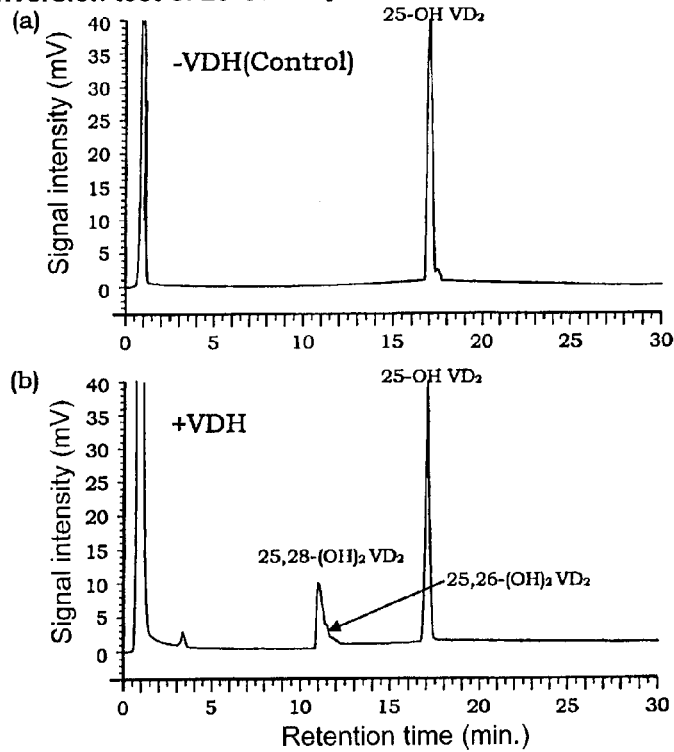

[Fig. 13]
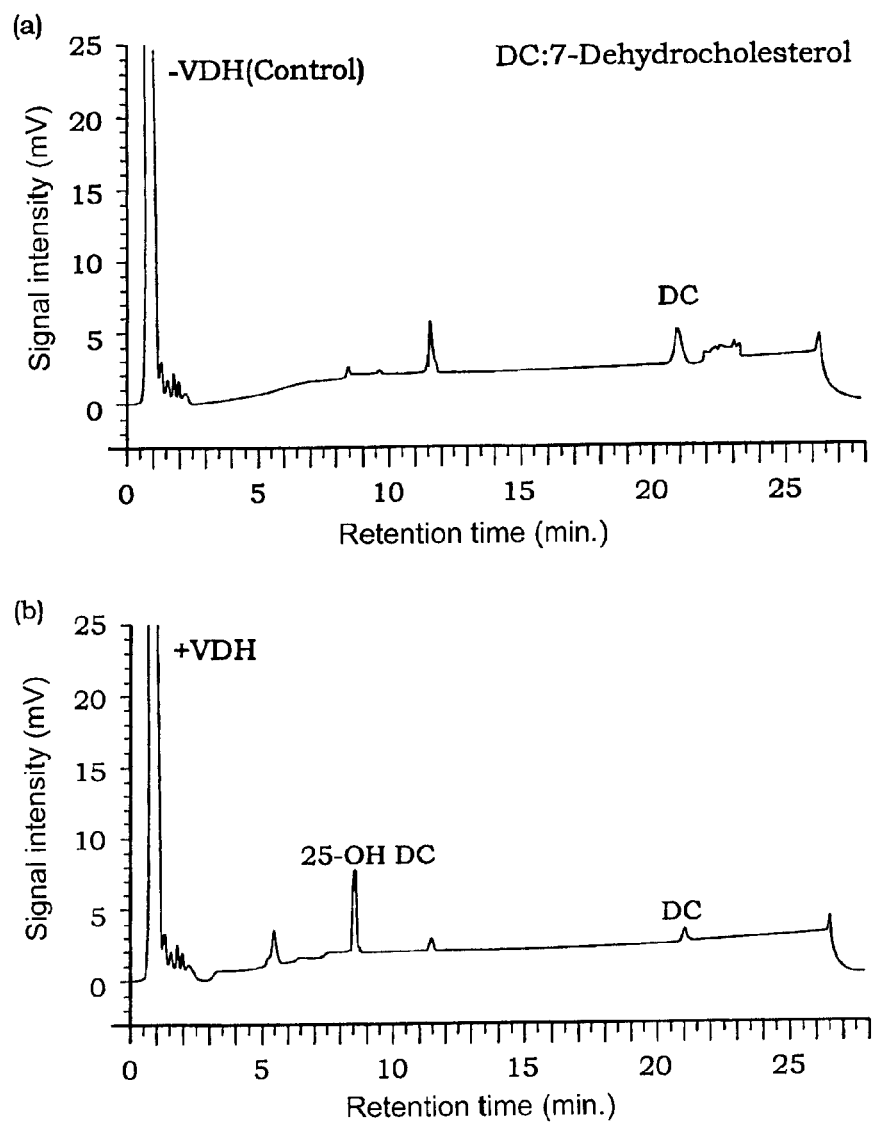

SEQUENCE LISTING

```
<160> NUMBER OF SEQ ID NOS: 26

<210> SEQ ID NO 1
<211> LENGTH: 2011
<212> TYPE: DNA
<213> ORGANISM: Pseudonocardia autotrophica
<220> FEATURE:
<221> NAME/KEY: CDS
<222> LOCATION: (320)..(1531)
<223> OTHER INFORMATION:

<400> SEQUENCE: 1
gcgctcgggc tggaccggat cggcgaggtg acgacgctgg ggctgcgctc ggtgcggacc         60
gcatgggccg ggctgcggac gttcgcccg gaccgggccc cggtgctggg ggagtggccc         120
gatcatcccg ggttccactt cgtcgccggc cagggtggat ccggtatcga gtcggctccg        180
gcgctggccg cgctggcagc gtcgatgatc gtcgggcggc cggcgcccgc cgatgtcgcg        240
ctcgatcccg ctgtgtgctc ggtcactcgt ctccggtgac gtaagcgcgc gcttacgtcg        300
cgctggcacg atggggccc atg gcg ctg acc acc acc ggc acc gag cag cac         352
                      Met Ala Leu Thr Thr Thr Gly Thr Glu Gln His
                       1               5                  10 gac ctg ttc tcg ggc acc ttc tgg cag aac ccg cat ccc gcc tac gcg          400
Asp Leu Phe Ser Gly Thr Phe Trp Gln Asn Pro His Pro Ala Tyr Ala
             15                  20                  25 gca ctc cgt gcc gag gat ccg gta cgc aag ctc gcg ctg ccg gac ggg          448
Ala Leu Arg Ala Glu Asp Pro Val Arg Lys Leu Ala Leu Pro Asp Gly
         30                  35                  40 ccg gtc tgg ctg ctc acc cgc tac gcc gac gtg cgc gag gcg ttc gtc          496
```

```
                    -continued

Pro Val Trp Leu Leu Thr Arg Tyr Ala Asp Val Arg Glu Ala Phe Val
    45                  50                  55 gat ccg cgc ctg tcg aag gac tgg cgc cac acg ctg ccc gag gac cag      544
Asp Pro Arg Leu Ser Lys Asp Trp Arg His Thr Leu Pro Glu Asp Gln
60                  65                  70                  75 cgg gcg gac atg ccg gcc acg ccg acg ccg atg atg atc ctg atg gat      592
Arg Ala Asp Met Pro Ala Thr Pro Thr Pro Met Met Ile Leu Met Asp
                80                  85                  90 ccg ccg gat cac acc cgg ctg cgc aag ctg gtc ggc agg tcg ttc acc      640
Pro Pro Asp His Thr Arg Leu Arg Lys Leu Val Gly Arg Ser Phe Thr
            95                  100                 105 gtc cgc cgg atg aac gag ctg gag ccg cgg atc acc gag atc gcc gac      688
Val Arg Arg Met Asn Glu Leu Glu Pro Arg Ile Thr Glu Ile Ala Asp
        110                 115                 120 ggc ctg ctc gcc ggc ctg ccc acc gac ggc ccg gtc gac ctg atg cgc      736
Gly Leu Leu Ala Gly Leu Pro Thr Asp Gly Pro Val Asp Leu Met Arg
    125                 130                 135 gag tac gcg ttc cag atc ccg gta cag gtg atc tgc gag ctg ctc ggg      784
Glu Tyr Ala Phe Gln Ile Pro Val Gln Val Ile Cys Glu Leu Leu Gly
140                 145                 150                 155 gtg ccc gcc gag gac cgc gac gac ttc tcc gcg tgg tcg tcg gtg ctg      832
Val Pro Ala Glu Asp Arg Asp Asp Phe Ser Ala Trp Ser Ser Val Leu
                160                 165                 170 gtc gac gac tcg ccg gcc gac gac aag aac gcg gcc atg ggc aag ctg      880
Val Asp Asp Ser Pro Ala Asp Asp Lys Asn Ala Ala Met Gly Lys Leu
            175                 180                 185 cac ggc tac ctg tcc gac ctg ctg gag cgc aag cgc acc gag ccc gac      928
His Gly Tyr Leu Ser Asp Leu Leu Glu Arg Lys Arg Thr Glu Pro Asp
        190                 195                 200 gac gcg ctg ttg tcg tcg ctg ctg gcg gtg tcc gac gag gac ggc gac      976
Asp Ala Leu Leu Ser Ser Leu Leu Ala Val Ser Asp Glu Asp Gly Asp
    205                 210                 215 cgg ctc tcc cag gag gag ctc gtc gcg atg gcg atg ctg ctg ctg atc     1024
Arg Leu Ser Gln Glu Glu Leu Val Ala Met Ala Met Leu Leu Leu Ile
220                 225                 230                 235 gcc ggg cac gag acg acg gtc aac ctg atc ggc aac ggc gtc ctc gcc     1072
Ala Gly His Glu Thr Thr Val Asn Leu Ile Gly Asn Gly Val Leu Ala
                240                 245                 250 ctg ctc acg cac ccc gac cag cgg aag ctg ctg gcc gag gac ccg tcg     1120
Leu Leu Thr His Pro Asp Gln Arg Lys Leu Leu Ala Glu Asp Pro Ser
            255                 260                 265 ctg atc agc tcg gcg gtc gag gag ttc ctg cgg ttc gac tct ccc gtc     1168
Leu Ile Ser Ser Ala Val Glu Glu Phe Leu Arg Phe Asp Ser Pro Val
        270                 275                 280 tcg cag gcc ccg atc cgg ttc acc gcg gag gac gtc acc tac tcc ggc     1216
Ser Gln Ala Pro Ile Arg Phe Thr Ala Glu Asp Val Thr Tyr Ser Gly
    285                 290                 295 gtg acc atc ccg gcc ggc gag atg gtc atg ctc ggg ctg gcc gcc gcc     1264
Val Thr Ile Pro Ala Gly Glu Met Val Met Leu Gly Leu Ala Ala Ala
300                 305                 310                 315 aac cgg gac gcc gac tgg atg ccc gag ccg gac cgg ctc gac atc acc     1312
Asn Arg Asp Ala Asp Trp Met Pro Glu Pro Asp Arg Leu Asp Ile Thr
                320                 325                 330 cgg gac gcc tcc ggc ggg gtg ttc ttc ggg cac ggc atc cac ttc tgc     1360
Arg Asp Ala Ser Gly Gly Val Phe Phe Gly His Gly Ile His Phe Cys
            335                 340                 345 ctc ggt gcc cag ctg gcc cgg ctg gag ggc cgg gtc gcg atc gga cgg     1408
Leu Gly Ala Gln Leu Ala Arg Leu Glu Gly Arg Val Ala Ile Gly Arg
        350                 355                 360 ctg ttc gcc gat cgc ccg gag ctg gcg ctc gcg gtc ggc ctc gac gag     1456
```

```
Leu Phe Ala Asp Arg Pro Glu Leu Ala Leu Ala Val Gly Leu Asp Glu
    365                 370                 375 ctg gtc tac cgg gag tcg acg ctg gtc cgg ggg ctg tcg agg atg ccg      1504
Leu Val Tyr Arg Glu Ser Thr Leu Val Arg Gly Leu Ser Arg Met Pro
380                 385                 390                 395 gtg acg atg ggg ccg cgc agc gcc tga tcccgttcgc ggacgggccg            1551
Val Thr Met Gly Pro Arg Ser Ala
                400 ggcggcccgt ccgcgagtac ggtcagccgc tcagtggtgc cccgtcttc tcccgcacct    1611 cgtcggcggt gacgccggga gcggtctcga ccagcgcgag ccgcccggg gtgacgtcga    1671 tgacggcgag atcggtgacg atccgggtga cgcagcccag cccggtgatg ggcaggctgc   1731 acgactcgac gatcttgggc gtgccgtcgc gggacacgtg gtccatcatc acgatgacgg   1791 tgcgggcgcc gtgcacgagg tccatcgcgc cgcccatccc cttgatcatc ttcccgggca   1851 cggcccagtt ggcgagatcg ccgttggcgg cgacctgcat gccgccgagc acggcgacgt   1911 cgagcttccc ggcgcggatc tgggcgaagc tgtccgagga gccgaagtag gcggcgccgt   1971 cgttgacggt gacggtctcc ttgcccgcgt tgatcaggtc                         2011

<210> SEQ ID NO 2
<211> LENGTH: 403
<212> TYPE: PRT
<213> ORGANISM: Pseudonocardia autotrophica

<400> SEQUENCE: 2

Met Ala Leu Thr Thr Thr Gly Thr Glu Gln His Asp Leu Phe Ser Gly
1               5                   10                  15

Thr Phe Trp Gln Asn Pro His Pro Ala Tyr Ala Ala Leu Arg Ala Glu
            20                  25                  30

Asp Pro Val Arg Lys Leu Ala Leu Pro Asp Gly Pro Val Trp Leu Leu
        35                  40                  45

Thr Arg Tyr Ala Asp Val Arg Glu Ala Phe Val Asp Pro Arg Leu Ser
    50                  55                  60

Lys Asp Trp Arg His Thr Leu Pro Glu Asp Gln Arg Ala Asp Met Pro
65                  70                  75                  80

Ala Thr Pro Thr Pro Met Met Ile Leu Met Asp Pro Asp His Thr
                85                  90                  95

Arg Leu Arg Lys Leu Val Gly Arg Ser Phe Thr Val Arg Arg Met Asn
            100                 105                 110

Glu Leu Glu Pro Arg Ile Thr Glu Ile Ala Asp Gly Leu Leu Ala Gly
        115                 120                 125

Leu Pro Thr Asp Gly Pro Val Asp Leu Met Arg Glu Tyr Ala Phe Gln
    130                 135                 140

Ile Pro Val Gln Val Ile Cys Glu Leu Leu Gly Val Pro Ala Glu Asp
145                 150                 155                 160

Arg Asp Asp Phe Ser Ala Trp Ser Ser Val Leu Val Asp Ser Pro
            165                 170                 175

Ala Asp Asp Lys Asn Ala Ala Met Gly Lys Leu His Gly Tyr Leu Ser
        180                 185                 190

Asp Leu Leu Glu Arg Lys Arg Thr Glu Pro Asp Ala Leu Leu Ser
    195                 200                 205

Ser Leu Leu Ala Val Ser Asp Glu Asp Gly Asp Arg Leu Ser Gln Glu
        210                 215                 220

Glu Leu Val Ala Met Ala Met Leu Leu Leu Ile Ala Gly His Glu Thr
225                 230                 235                 240
```

```
Thr Val Asn Leu Ile Gly Asn Gly Val Leu Ala Leu Thr His Pro
            245                 250                 255
Asp Gln Arg Lys Leu Leu Ala Glu Pro Ser Leu Ile Ser Ser Ala
        260                 265                 270
Val Glu Glu Phe Leu Arg Phe Asp Ser Pro Val Ser Gln Ala Pro Ile
    275                 280                 285
Arg Phe Thr Ala Glu Asp Val Thr Tyr Ser Gly Val Thr Ile Pro Ala
290                 295                 300
Gly Glu Met Val Met Leu Gly Leu Ala Ala Asn Arg Asp Ala Asp
305                 310                 315                 320
Trp Met Pro Glu Pro Asp Arg Leu Asp Ile Thr Arg Asp Ala Ser Gly
                325                 330                 335
Gly Val Phe Phe Gly His Gly Ile His Phe Cys Leu Gly Ala Gln Leu
            340                 345                 350
Ala Arg Leu Glu Gly Arg Val Ala Ile Gly Arg Leu Phe Ala Asp Arg
        355                 360                 365
Pro Glu Leu Ala Leu Ala Val Gly Leu Asp Glu Leu Val Tyr Arg Glu
    370                 375                 380
Ser Thr Leu Val Arg Gly Leu Ser Arg Met Pro Val Thr Met Gly Pro
385                 390                 395                 400
Arg Ser Ala

<210> SEQ ID NO 3
<211> LENGTH: 24
<212> TYPE: PRT
<213> ORGANISM: Artificial Sequence
<220> FEATURE:
<223> OTHER INFORMATION: VDH

<400> SEQUENCE: 3

Ala Leu Gly Thr Glu Gln His Asp Leu Phe Ser Gly Phe Phe Trp Gln
1               5                   10                  15
Asn Pro Gln Pro Pro Tyr Ala Ala
            20

<210> SEQ ID NO 4
<211> LENGTH: 12
<212> TYPE: PRT
<213> ORGANISM: Artificial Sequence
<220> FEATURE:
<223> OTHER INFORMATION: VDH-i

<400> SEQUENCE: 4

Leu His Gly Tyr Leu Ser Asp Leu Leu Glu Arg Lys
1               5                   10

<210> SEQ ID NO 5
<211> LENGTH: 20
<212> TYPE: DNA
<213> ORGANISM: Artificial Sequence
<220> FEATURE:
<223> OTHER INFORMATION: VDH-I-1F
<220> FEATURE:
<221> NAME/KEY: misc_feature
<222> LOCATION: (18)..(18)
<223> OTHER INFORMATION: n=a, t, g, and c

<400> SEQUENCE: 5
ttcttctggc agaacccnca                                           20

<210> SEQ ID NO 6
<211> LENGTH: 20
```

```
<212> TYPE: DNA
<213> ORGANISM: Artificial Sequence
<220> FEATURE:
<223> OTHER INFORMATION: VDH-I-1R
<220> FEATURE:
<221> NAME/KEY: misc_feature
<222> LOCATION: (6)..(6)
<223> OTHER INFORMATION: s=g and c
<220> FEATURE:
<221> NAME/KEY: misc_feature
<222> LOCATION: (18)..(18)
<223> OTHER INFORMATION: y=c and t
<220> FEATURE:
<221> NAME/KEY: misc_feature
<222> LOCATION: (15)..(15)
<223> OTHER INFORMATION: y=c and t

<400> SEQUENCE: 6
gagaasaggt cgtgytgytc                                         20

<210> SEQ ID NO 7
<211> LENGTH: 30
<212> TYPE: DNA
<213> ORGANISM: Artificial Sequence
<220> FEATURE:
<223> OTHER INFORMATION: VDH-I-2F

<400> SEQUENCE: 7
ggccgacgac aagaacgcgg ccatgggcaa                              30

<210> SEQ ID NO 8
<211> LENGTH: 30
<212> TYPE: DNA
<213> ORGANISM: Artificial Sequence
<220> FEATURE:
<223> OTHER INFORMATION: VDH-I-2R

<400> SEQUENCE: 8
ggcgagtcgt cgaccagcac cgacgaccac                              30

<210> SEQ ID NO 9
<211> LENGTH: 30
<212> TYPE: DNA
<213> ORGANISM: Artificial Sequence
<220> FEATURE:
<223> OTHER INFORMATION: VDH-1F

<400> SEQUENCE: 9 gcccccata tggcgctgac caccaccggc                               30

<210> SEQ ID NO 10
<211> LENGTH: 30
<212> TYPE: DNA
<213> ORGANISM: Artificial Sequence
<220> FEATURE:
<223> OTHER INFORMATION: VDH-1R

<400> SEQUENCE: 10
gccactagtt caggcgctgc gcggccccat                              30

<210> SEQ ID NO 11
<211> LENGTH: 30
<212> TYPE: DNA
<213> ORGANISM: Artificial Sequence
<220> FEATURE:
<223> OTHER INFORMATION: VDH-2R

<400> SEQUENCE: 11
gccctcgagg gcgctgcgcg gccccatcgt                              30
```

<210> SEQ ID NO 12
<211> LENGTH: 30
<212> TYPE: DNA
<213> ORGANISM: Artificial Sequence
<220> FEATURE:
<223> OTHER INFORMATION: ThcCD-1F

<400> SEQUENCE: 12
gccaagctta tgcctaccgt cacctacgtt                                    30

<210> SEQ ID NO 13
<211> LENGTH: 33
<212> TYPE: DNA
<213> ORGANISM: Artificial Sequence
<220> FEATURE:
<223> OTHER INFORMATION: ThcCD-1R

<400> SEQUENCE: 13
gccggatcct catgacgcca ccacctgacg ctc                                33

<210> SEQ ID NO 14
<211> LENGTH: 30
<212> TYPE: DNA
<213> ORGANISM: Artificial Sequence
<220> FEATURE:
<223> OTHER INFORMATION: ThcCD IPCR-1F

<400> SEQUENCE: 14
atccttgcca ccgaaatgcc gctcaccccc                                    30

<210> SEQ ID NO 15
<211> LENGTH: 30
<212> TYPE: DNA
<213> ORGANISM: Artificial Sequence
<220> FEATURE:
<223> OTHER INFORMATION: ThcCD IPCR-1R

<400> SEQUENCE: 15
ctttcgtgcc gccatgtggt cgcggggctt                                    30

<210> SEQ ID NO 16
<211> LENGTH: 30
<212> TYPE: DNA
<213> ORGANISM: Artificial Sequence
<220> FEATURE:
<223> OTHER INFORMATION: ThcCD-2F

<400> SEQUENCE: 16 gcccccata tgcctaccgt cacctacgtt                                     30

<210> SEQ ID NO 17
<211> LENGTH: 30
<212> TYPE: DNA
<213> ORGANISM: Artificial Sequence
<220> FEATURE:
<223> OTHER INFORMATION: ThcCD-3F

<400> SEQUENCE: 17
gcctctagag tctagaaata attttgttta                                    30

<210> SEQ ID NO 18
<211> LENGTH: 30
<212> TYPE: DNA
<213> ORGANISM: Artificial Sequence
<220> FEATURE:
<223> OTHER INFORMATION: ThcCD-2R

```
<400> SEQUENCE: 18
gccgaattct catgacgcca ccacctgacg                               30

<210> SEQ ID NO 19
<211> LENGTH: 30
<212> TYPE: DNA
<213> ORGANISM: Artificial Sequence
<220> FEATURE:
<223> OTHER INFORMATION: ThcCD IPCR-2F

<400> SEQUENCE: 19
tacgttcacc ctgatggaac caagcatgag                               30

<210> SEQ ID NO 20
<211> LENGTH: 30
<212> TYPE: DNA
<213> ORGANISM: Artificial Sequence
<220> FEATURE:
<223> OTHER INFORMATION: ThcCD IPCR-2R

<400> SEQUENCE: 20
ggtgacggta ggcatgtgta tatctccttc                               30

<210> SEQ ID NO 21
<211> LENGTH: 30
<212> TYPE: DNA
<213> ORGANISM: Artificial Sequence
<220> FEATURE:
<223> OTHER INFORMATION: ThcCD-4F

<400> SEQUENCE: 21
gccactagtg tctagaaata attttgttta                               30

<210> SEQ ID NO 22
<211> LENGTH: 30
<212> TYPE: DNA
<213> ORGANISM: Artificial Sequence
<220> FEATURE:
<223> OTHER INFORMATION: ThcCD-3R

<400> SEQUENCE: 22
gccagatctt catgacgcca ccacctgacg                               30

<210> SEQ ID NO 23
<211> LENGTH: 23
<212> TYPE: DNA
<213> ORGANISM: Artificial Sequence
<220> FEATURE:
<223> OTHER INFORMATION: Linker NSBS-1

<400> SEQUENCE: 23
tatggcacta gtgcagatct gcg                                      23

<210> SEQ ID NO 24
<211> LENGTH: 25
<212> TYPE: DNA
<213> ORGANISM: Artificial Sequence
<220> FEATURE:
<223> OTHER INFORMATION: Linker NSBS-2

<400> SEQUENCE: 24
tcgacgcaga tctgcactag tgcca                                    25

<210> SEQ ID NO 25
<211> LENGTH: 32
```

```
<212> TYPE: DNA
<213> ORGANISM: Artificial Sequence
<220> FEATURE:
<223> OTHER INFORMATION: VDH-101F

<400> SEQUENCE: 25
cggcatatgg cgctgaccac caccggcacc ga                          32

<210> SEQ ID NO 26
<211> LENGTH: 35
<212> TYPE: DNA
<213> ORGANISM: Artificial Sequence
<220> FEATURE:
<223> OTHER INFORMATION: VDH-106R

<400> SEQUENCE: 26
gcactagttc aggcgctgcg cggccccatc gtcac                       35
```

HYDROXYLASE GENE AND USE THEREOF

TECHNICAL FIELD

The present invention relates to hydroxylase such as vitamin D, a gene that codes for hydroxylase, an isolation method thereof, transgenic organisms wherein the genes are introduced, and a method for producing a hydroxide of vitamin D or the like (e.g., 25-hydroxy vitamin $D_3$ and 1α,25-dihydroxy vitamin $D_3$).

BACKGROUND ART

Vitamin D is an essential fat-soluble vitamin group mainly for higher organisms and formed by biosynthesis from cholesterol. Vitamin D plays important roles in organisms due to its wide variety of physiological activities such as stimulating absorption of calcium, metabolic stimulation, inducing cellar differentiation and immune regulation and the like.

In a main vitamin D biosynthetic pathway in human beings, after 7-dehydrocholesterol (provitamin $D_3$) is first synthesized from cholesterol, vitamin $D_3$ is produced in the skin by ultraviolet ray and thermal reaction. 25-hydroxy vitamin $D_3$ is obtained by 25-hydroxylation of vitamin $D_3$ by mitochondrially-located cytochrome P450 (CYP27A1) in the liver. Then, through further 1α hydroxylation by another cytochrome P450 (CYP27B1) in the proximal convoluted tubule, 1α,25-dihydroxy vitamin $D_3$ (activated vitamin $D_3$) is produced. It is confirmed that this substance regulates expression of specific nuclear genes involved in expression of physiological activities by being bound to an intracellular receptor.

Accordingly, when the liver or kidney becomes dysfunctional, normal vitamin D metabolism may be inhibited. Regarding the patient with such symptoms, the level of 25-hydroxyvitamin $D_3$ or 1α,25-dihydroxy vitamin $D_3$ in the blood may extremely reduces, and it is necessary for treatment to supplement 25-hydroxyvitamin $D_3$ or 1α,25-dihydroxy vitamin $D_3$ by the administration.

Meanwhile, rickets is known as being caused by a low level of 1α,25-dihydroxy vitamin $D_3$ due to dysfunction of hydroxylation resulting from a congenital genetic mutation in cytochromes which is involved in hydroxylation of vitamin $D_3$. 1α,25-dihydroxy vitamin $D_3$ and analogous compounds having similar physiological activities have significant importance as therapeutic agents for diseases due to lack of 1α,25-dihydroxy vitamin $D_3$ including acquired rickets and osteoporosis as well as congenital rickets.

Furthermore, owing to various physiological activities of the vitamin D group, various derivatives thereof have been studied as candidate agents and developments of antineoplastic agent, antipsoriatic agent, immunostimulating agent and the like are also expected. Seen from this view point, hydroxylation is important as one method for modifying by derivatizing the vitamin D group. In such a case, the importance of hydroxylation is not limited to 1α- and 25-positions but great needs may arise for hydroxylation at other positions. To meet such needs for manufacturing and discovering drugs, there has been rising demand in the pharmaceutical industry for improving production method of a hydroxide of vitamin D and the like in order to manufacture and supply a hydroxide of vitamin D more efficiently at lower cost.

Referring to 1α,25-dihydroxy vitamin $D_3$, which has particularly strong physiological activities and therefore has high value among the vitamin D group, the production method thereof includes an organic synthesis method, a method using cytochromes P450 of human beings and a method using hydroxylase of microorganisms. Among these, a method for synthesizing 1α,25-dihydroxy vitamin $D_3$ from cholesterol through 17 steps has been known in the organic synthesis method. In the method using cytochromes P450 of human beings, biological and biochemical findings have been accumulated relating to genes involved, technology for expression and the nature of cytochromes P450 enzyme (Review by T. Sakaki et al., Frontiers in Bioscience, 10, 119-134, 2005; Non-patent document 1). However, both of the two methods are quite unsuitable for practical use owing to high production costs and low productivity.

Meanwhile, a method using hydroxylase of microorganisms is a relatively promising production method.

For example, Sasaki et al. of Taisho Pharmaceutical Co., Ltd. isolated *actinomycete, Pseudonocardia autotrophica*, producing 1α,25-dihydroxy vitamin $D_3$ by hydroxylation of vitamin $D_3$ in the course of search for microorganisms (J. Sasaki et al., Applied Microbiology and Biotechnology, 38, 152-157, 1992; Non-patent document 2). As a result of improvement in breeding of the strain and development of the production processes at Mercian Corporation, the method for producing 1α,25-dihydroxy vitamin $D_3$ by microbial conversion was established (K. Takeda et al., J. Ferment. Bioeng., 78, 380-382, 1994: Non-patent document 3) and has been put to practical use.

Laid-Open Japanese Patent Publication No. 2003-325175 (Patent Document 1) by Mitsubishi Chemical Corporation discloses a method for producing 25-hydroxy vitamin $D_3$ by hydroxylation at 25-position of vitamin $D_3$ using *Bacillus megaterium*. However, the amount of accumulated 25-hydroxy vitamin $D_3$ in the culture medium is small by this method and the publication does not describe the production of 1α,25-dihydroxy vitamin $D_3$.

Regarding the finding on a gene for the vitamin $D_3$ hydroxylase derived from microorganisms, a gene for vitamin $D_3$ hydroxylase at 25-position derived from *Pseudonocardia autotrophica* is reported in 1994 (H. Kawauchi et al., Biochimica et Biophysica Acta, 179-183, 1994; Non-patent document 4), which is apparently different from the gene of the present invention in terms of the nucleotide sequence and the characterization of the enzyme encoded by the gene. Also, Sawada et al. reported in 2004 that P450SU-1 (CYP105A1) encoded by cytochromes P450 gene derived from *actinomycete, Streptomyces griseolus* ATCC 11796, showed weak activity for hydroxylation of vitamin $D_3$ to 25-hydroxy vitamin $D_3$ and that of 25-hydroxy vitamin $D_3$ to 1α,25-hydroxy vitamin $D_3$ D. P. O'Keefe et al., Arch. Microbiol., 149, 406-412, 1988; Non-patent document 5).

Thus, various findings have been shown on microbial transformation of vitamin $D_3$ by hydroxylation. Among these, only the method for producing 1α,25-dihydroxy vitamin $D_3$ from vitamin $D_3$ using *Pseudonocardia autotrophica* strain for transformation has been put into practical use industrially (Laid-open Japanese patent publication H02-469 (U.S. Pat. No. 4,892,821); Patent document 2 and Laid-open Japanese patent publication H02-231089; Patent document 3). However, issues to be solved by improvement for a more efficient production process still remain in this method.

[Non-patent document 1] Review by T. Sakaki et al., Frontiers in Bioscience, 10, 119-134, 2005
[Non-patent document 2] J. Sasaki et al., Applied Microbiology and Biotechnology, 38, 152-157, 1992
[Non-patent document 3] K. Takeda et al., J. Ferment. Bioeng., 78, 380-382, 1994
[Non-patent document 4] H. Kawauchi et al., Biochimica et Biophysica Acta, 179-183, 1994
[Non-patent document 5] D. P. O'Keefe et al., Arch. Microbiol., 149, 406-412, 1988

[Patent document 1] Laid-Open Japanese Patent Publication No. 2003-325175
[Patent document 2] Laid-open Japanese patent publication H02-469
[Patent document 3] Laid-open Japanese patent publication H02-231089

DISCLOSURE OF THE INVENTION

Problems to be Solved by the Invention

In the above-mentioned method for producing 1α,25-dihydroxy vitamin $D_3$ from vitamin $D_3$, after incubating *Pseudonocardia autotrophica* in a fermenter, vitamin $D_3$ is added to the culture medium as a reactive substrate so as to conduct a reaction by the action of hydroxylase in the bacteria to thereby recover and purify 1α,25-dihydroxy vitamin $D_3$ accumulated in the culture medium.

This production method requires a long-term production due to the use of *actinomycete* which has a long growing period. In addition, the action for vitamin $D_3$ transformation of the bacteria includes not only the aimed hydroxylation but also undesirable side reactions. Such reactions include, for example, hydroxylation at 26-position and hydroxylation at 24-position. Also, the transforming bacteria has a degradation activity of vitamin $D_3$ and 1α,25-dihydroxy vitamin $D_3$ as substrates.

In particular, degradation of 1α,25-dihydroxy vitamin $D_3$ is a very important issue directly affecting the accumulated amount of the objective product. In addition to this, the presence of byproducts leads to the increase in the purification steps for recovering 1α,25-dihydroxy vitamin $D_3$ from the culture medium, which results in lowering the product yield. Given these circumstances, suppressing side reactions and increasing the accumulated amount of the objective product have been major issues in the conventional production method in order to achieve more efficient production method.

Means to Solve the Problem

As a result of an intensive study to improve the production method, the present inventors first cloned a gene encoding the enzyme which involves in hydroxylation at 1α- and 25-positions of vitamin $D_3$ from *Pseudonocardia autotrophica* NBRC12743 strain having substantial capability for hydroxylation of vitamin $D_3$. Subsequently, the gene is expressed into a host cell such as *Rhodococcus erythropolis* and *Escherichia coli*, which has no or few side reactions and little degradation activity in order to accomplish the present invention.

The present invention enabled breakaway from conventional trial within the limitation for regulating the complicated physiological and metabolic mechanism of *Pseudonocardia autotrophica* to the advantage of production. That is, isolation of a gene for the hydroxylase for hydroxylation at 1α- and 25-positions enabled abundant expression of the hydroxylase in an optimum host for production using genetic engineering technology and thereby to solve the conventional technical problems. In addition, while the technologies available for breeding a strain for transformation include improvement of the enzyme function through an advanced gene expression system and gene modification, these technologies would not be possible without the use of the gene of the present invention. The hydroxylase has novel properties which are quite suitable for industrial use among the hydroxylase for vitamin D and the like reported up to the present. Consequently, the present invention can provide a method for producing the hydroxide of vitamin D or the like, which is industrially quite useful and efficient.

That is, the present invention relates to vitamin $D_3$ hydroxylase, a gene encoding that hydroxylase, an isolation method thereof, transgenic organisms wherein the genes are introduced, and a method for producing a hydroxide of vitamin D or the like (e.g., 25-hydroxy vitamin $D_3$ and 1α,25-hydroxy vitamin $D_3$) as follow:

1. A gene derived from *actinomycetes* encoding a hydroxylase capable of hydroxylation of at least one of vitamin $D_3$, vitamin $D_2$ and 7-dihydrocholesterol.
2. The hydroxylase gene as described in 1 above, which is derived from *Pseudonocardia autotrophica*.
3. The hydroxylase gene as described in 2 above, which is derived from *Pseudonocardia autotrophica* NBRC12743 strain.
4. The hydroxylase gene as described in 1 above, which is coded from 320th to 1531st nucleotide sequence represented by sequence ID No. 1.
5. A variant or a homologous gene of the hydroxylase gene as described in 4 above represented by the following (1) or (2):
   (1) A variant of the hydroxylase gene described in 4 above, which hybridizes with the DNA coding nucleotide sequence described in 4 above under stringent conditions and the hydroxylation activity against the vitamin D compounds and the substrate spectrum of the hydroxylase coded by the variant are regarded equivalent as those of the hydroxylase coded by the hydroxylase gene described in above 4; and
   (2) A homologous gene with the hydroxylase gene described in 4 above, which is derived from microorganisms other than *Pseudonocardia autotrophica* NBRC12743 strain and codes polypeptide having hydroxylation activity against the vitamin D compounds, and hybridizes with the DNA coding nucleotide sequence described in 4 above under stringent conditions and the hydroxylation activity against the vitamin D compounds and the substrate spectrum of the hydroxylase coded by the variant are regarded equivalent as those of the hydroxylase coded by the hydroxylase gene described in above 4.
6. A variant or a homologous gene of the hydroxylase gene as described in 5 above, obtained from *actinomycete* using at least 20 consecutive nucleotides in the 320th to 1531st nucleotide sequence represented by sequence ID No. 1 or the complementary strand as a probe.
7. A hydroxylase coded by the gene described in any one of 1 to 6 above.
8. A hydroxylase containing the amino acid sequence represented by sequence ID No. 2.
9. Transgenic organisms obtained by introducing the gene described in any one of 1 to 6 above into a host organism.
10. The transgenic organisms as described in 9 above, the host organism of which is *Escherichia coli* or *actinomycete*.
11. A method for producing a hydroxide of the vitamin D compounds; precursor, metabolite, derivative or steroids thereof; or a modified compound thereof, wherein a conversion reaction is conducted by adding the vitamin D compounds or 7-dehydrocholesterol as a reactive substrate to the culture medium or a processed goods thereof.
12. The method for producing a hydroxide as described in 11 above which coexpresses hydroxylase gene and Redox Partner genes in the transgenic organisms described in 9 or 10 above.
13. The method for producing a hydroxide as described in 12 above, wherein the Redox Partner genes are represented by any one of the following (1) to (3):

(1) thcCD gene;
(2) a variant of the thcCD gene described in (1) above, which hybridizes with the DNA coding nucleotide sequence of the thcCD gene under stringent conditions, wherein the redox partner coded by the variant is capable of transferring electrons to the hydroxylase coded from 320th to 1531st nucleotide sequence represented by sequence ID No. 1;
(3) a homologous gene with the thcCD gene, which is derived from microorganisms other than *Rhodococcus erythropolis* NI86/21 strain and hybridizes with the DNA coding nucleotide sequence of the thcCD gene of (1) above under stringent conditions, wherein the redox partner coded by the homologous gene is capable of transferring electrons to the hydroxylase coded from 320th to 1531st nucleotide sequence represented by sequence ID No. 1.
14. The method for producing the hydroxide as described in any one of 11 to 13 above, wherein the hydroxide of the vitamin D or the like is 1α,25-dihydroxy vitamin $D_3$.
15. The method for producing the hydroxide as described in any one of 11 to 13 above, wherein the hydroxide of the vitamin D or the like is 25-dihydroxy vitamin $D_3$.
16. The method for producing the hydroxide as described in any one of 11 to 13 above, wherein the hydroxide of the vitamin D or the like is 1α,25-dihydroxy vitamin $D_2$.
17. A method for obtaining hydroxylase genes from genomic DNA or cDNA of microorganisms using at least 20 consecutive nucleotides in the nucleotide sequence represented by sequence ID No. 1 or the complementary strand as a probe.

Best Mode for Carrying out the Invention

In the present specification, the gene for the vitamin D or the like hydroxylase of the present invention may refer not only to the gene coded by the DNA sequence represented by sequence ID No. 1 derived *Pseudonocardia autotrophica* NBRC12743 strain but also a variant and a homologous gene thereof (hereinafter they may be abbreviated as "vdh genes"). The vdh gene can be cloned by PCR (polymerase chain reaction) using the oligo DNA primer synthesized based on the N-terminal amino acid or the internal amino acid sequence of the isolated hydroxylase of vitamin D or the like (hereinafter it may be abbreviated as "VDH") from the cultured *Pseudonocardia autotrophica* or the closely-related microorganisms and conducting hydroxylase.

"Vitamin D or the like" used in the present invention is recognized as a substrate by the VDH of the present invention; indicates those to which an oxygen atom can be added to a carbon atom at 1α-position, 25-position and another position; and includes the following substances:
(1) vitamin D group such as vitamin $D_3$ and vitamin $D_2$,
(2) precursors, metabolites and other derivatives of vitamin D or the like (which include 7-dehydrocholesterol, 25-hydroxy vitamin $D_3$ and 1α-dihydroxy vitamin $D_3$); and
(3) steroids or modified compounds thereof.

With respect to the strain to obtain the vdh gene of the present invention, any microorganisms can be used regardless species and kind of the strain as long as they are capable of hydroxylation of vitamin D or the like. However, *Pseudonocardia autotrophica* is preferable and more preferable examples include those strains listed in the following Table 1 in which the presence of the vdh gene is confirmed by the PCR method as well as the disclosed strains (see Laid-open Japanese Patent Publication Nos. H02-469 and H02-231089). The strains containing vdh genes are not limited to those listed in the Table. In the Table, *Pseudonocardia* is abbreviated as "P.".

TABLE 1

| Strains containing a vdh gene |
|---|
| *P. autotrophica* DSM535 |
| *P. autotrophica* DSM43082 |
| *P. autotrophica* DSM43083 |
| *P. autotrophica* DSM43084 |
| *P. autotrophica* DSM43085 |
| *P. autotrophica* DSM43086 |
| *P. autotrophica* DSM43087 |
| *P. autotrophica* DSM43088 |
| *P. autotrophica* DSM43090 |
| *P. autotrophica* DSM43091 |
| *P. autotrophica* DSM43093 |
| *P. autotrophica* DSM43094 |
| *P. autotrophica* DSM43095 |
| *P. autotrophica* DSM43096 |
| *P. autotrophica* DSM43097 |
| *P. autotrophica* DSM43098 |
| *P. autotrophica* DSM43099 |
| *P. autotrophica* DSM43100 |
| *P. autotrophica* DSM43101 |
| *P. autotrophica* DSM43102 |
| *P. autotrophica* DSM43103 |
| *P. autotrophica* DSM43104 |
| *P. autotrophica* DSM43105 |
| *P. autotrophica* DSM43106 |
| *P. autotrophica* DSM43107 |
| *P. autotrophica* DSM43108 |
| *P. autotrophica* DSM43128 |
| *P. autotrophica* DSM43129 |
| *P. autotrophica* DSM43558 |
| *P. autotrophica* ATCC13181 |
| *P. autotrophica* ATCC19727 |
| *P. autotrophica* ATCC33795 |
| *P. autotrophica* ATCC33796 |
| *P. autotrophica* ATCC33797 |
| *P. autotrophica* JCM4010 |
| *P. saturnea* IFO14499 |
| *P. saturnea* FERM BP2307 |
| *P. autotrophica* 4M1067 |

Generally, these strains can be cultured at 30° C. for about three days using a culture medium suitable for the culture of microorganisms in general such as L-liquid medium (1.0% of Bacto-tryptone, 0.5% of yeast extract and 0.5% sodium chloride) in order to prepare bacterial cells to purify DNA and enzymes.

Methods required for performing the invention of the present specification: e.g. experimental manipulations of microorganisms including genetic engineering techniques such as extraction of DNA, cloning and expression of genes, PCR, obtaining complete genome sequences by inverse PCR can be carried out according to the methods described in "Molecular Cloning" of the second edition. Also, the similar manipulations regarding *actinomycetes* in particular can be performed according to the methods described in the experiment manual authored by Kieser et al. (Practical *Streptomyces* Genetics, The John Innes Foundation, Norwich, England, 2000).

The above-mentioned article by Sawada et el. (N. Sawada et al., Biochemical and Biophysical Research Communications 320, 156-164, 2004) showed that the active component involved in hydroxylation was highly like cytochrome P450 monooxygenase. VDH was also considered to be cytochrome P450 from its characterization and known relevant information. The general method for purifying cytochrome P450 enzyme from the microbial fungus body can be performed according to the procedure described in the documents relating to P450SU-1 D. P. O'Keefe et al., Arch. Microbiol., 149, 406-412, 1988) or modified procedures thereof. That is, a cell-free extract of bacterial cells is prepared by French press treatment or ultrasonic fragmentation treatment after suspending the cells in an appropriate buffer solution. Then, by performing two- or three-steps of chromatographic purification, almost pure enzyme can be obtained. The columns can be used here include ion-exchange column chromatography, gel filtration column chromatography and affinity column chromatography.

Next, the gene coding the enzyme protein can be obtained according to the following procedures. That is, by subjecting the purified protein to SDS-PAGE (SDS polyacrylamide gel electrophoresis), proteins on the gel are transferred to a PVDF (polyvinylidene difuluoride) membrane and a band of the protein to be observed is cut off. Using this membrane as a sample of an amino acid sequence analyzer, the N-terminal amino acid sequence of the objective enzyme can be determined according to the Edman method. Also, using the polypeptide generated after the protease digestion in the same way, the internal amino acid sequence of the objective enzyme can be identified.

By conducting PCR using the primer synthesized based on the N-terminal amino acid sequence and the internal amino acid sequence, a fragment encoding the objective gene can be obtained. Judging from the region where the primer is constructed, this DNA fragment encodes the polypeptide from the N-terminal to a part of the amino acid sequence inside the gene, it is necessary to obtain a DNA fragment containing the entire gene. For this purpose, inverse PCR is performed to obtain the sequence information of the whole gene and then PCR is conducted to amplify the DNA fragment with the primers constructed from arbitrary both terminals or the coding region of the reedited sequence so as to ultimately obtain an objective fragment. The nucleotide sequence of the PCR-amplified DNA can be determined by a DNA sequence analyzer.

As explained in details in Example 6 described later, the vdh gene can be represented by the nucleotide sequence described in sequence ID No. 1 and encodes amino acid sequence of VDH described in sequence No. 2. An oxygen binding site and a heme binding site are present in the amino acid sequence of VDH as well as the internal amino acid sequence determined in Example 4, which confirms that VDH is a gene coding the purified enzyme. As a result of the homology search of the VDH amino acid sequence, the VDH sequence had 50% similarity to that of cytochrome P450RubU derived from *Streptomyces collinus* DSM 2012 and assumed to be cytochrome P450 belonging to CYP107 family.

Upon obtaining the vdh gene of the present invention, some problems have been revealed which are difficult to solve by usual methods the one skilled in the art may try.

One of the problems was that a shotgun cloning, which is a gene cloning method most often tried, was not effective. That is, individual clones of *Streptomyces lividance* having random recombinant DNA fragments of *Pseudonocardia autotrophica* constructed by using a host-vector system established with regard to *Streptomyces lividans* were screened using hydroxylation activity for vitamin $D_3$ as an index. However, though the screen test was performed for a number of the clones, it failed to obtain a clone having hydroxylation activity.

Later, it was found that there is strict specificity in the electron transfer cofactor protein which is essential VDH activity. In fact, while a reaction proceeds in a reconstituted protein synthesizing system containing ferredoxin derived from spinach, ferredoxin reductase and purified VDH, electron transfer reaction did not proceed in a synthesizing system containing putidaredoxin and putidaredoxin reductase derived from *Pseudomonas putida*, which is considered to be capable of transferring electrons to a number of *actinomycetes* P450.

In the present invention, the electron transfer cofactor protein which is essential for activating VDH may be referred to as "redox partner".

As a result, cloning of a gene encoding VDH was attempted by using the amino acid sequence information of the purified VDH as an another approach. Though the purification of VDH was difficult due to very low expression level of VDH in a cell, the inventors have found that VDH expression is induced by addition of cholesterol and have succeeded in preparation of VDH-enriched cells suitable for purification.

Contrary to all expectations, the activity was not detected with the cell-free extract prepared by cell disruption. As a result of studies, the activity was recovered by increasing salt concentration to a high level which is quite different from that of the ordinary reaction conditions of cytochrome P450 enzyme, which resulted in solving problems. Thus, the inventors went through a number of difficulties before they succeeded in the cloning of vdh genes but, as a result of intensive studies, they solved all the problems and accomplished the present invention.

By reproducing the method performed by the present inventors, the one skilled in the art not only can obtain vdh genes of the present invention but also can obtain vdh genes by common genetic engineering procedures for cloning the gene capable of hybridizing under stringent conditions by using the DNA sequence of the vdh gene represented by sequence ID No. 1 as a probe.

In the present specification, the term "genes capable of hybridizing under stringent conditions" means, for example, DNA obtained by the colony hybridization method, plaque hybridization method, southern hybridization method and the like using as a probe RNA or DNA having a part of sequence information of a gene. Specifically, the term defines the DNA obtained by performing hybridization at 65° C. under the presence of 0.7 to 1.0 M sodium chloride using a filter on which DNA derived from a colony or plaque is fixed, which shows a hybridizing signal even after washing the filter under 65° C. temperature condition.

In particular, when the homologous gene of the vdh gene to be obtained has high similarity: e.g. the homologous gene shows 90% identity compared to the nucleotide sequence of the vdh gene described in sequence ID No. 1, the vdh gene can be obtained by using as a probe the DNA sequence of the vdh gene described in sequence ID No. 1. A new vdh gene can be obtained by homology search of existing databases for a sequence having predetermined homology using the above-mentioned sequence or by performing PCR using a pair of primer which is synthesized based on the sequence. Such a probe is preferably at least 20 consecutive bases of the DNA sequence of the vdh gene described in sequence ID No. 1 or a complementary strand thereof.

The thus-obtained homologous gene having high homology may be referred to as a "homolog".

During the process of performing a series of genetic engineering manipulations such as recombination of vdh genes and gene expression, DNA modification such as deletion, substitution, addition or insertion of the DNA nucleotide sequence composition may be conducted for the purpose of modifying codon in the vdh gene of a foreign host, adding or deleting restriction enzyme sites or fusing specific polypeptide with VDH without impairing the functions and effects of the gene. The thus-structured DNA is defined as "a variant of DNA". In the present specification, "a variant of DNA" means DNA modified by deletion, substitution, addition, insertion or the like of the nucleotide sequence composition or a derivative thereof, which exhibits substantially equivalent effects of the original DNA though it may often accompany replacement of the coded amino acid sequence.

By cloning the obtained vdh gene into an appropriate vector and introducing it in a host, a transformant of the vdh gene of the present invention can be prepared. As a host, any living organism can be used as long as it enables stable maintenance and expression of the vdh gene. Recombinant plants containing activated vitamin $D_3$ can also be obtained by introducing the vdh gene into a plant cell. However, as a host, microorganisms are preferable, which are free from decomposition and side reactions, able to grow fast by an inexpensive culture method and easy to handle in a manufacturing setting.

Specific examples of a host to be used include not only *Escherichia coli*, *Bacillus* bacteria and *Pseudomonas* bacteria but also *actinomycetes* (which includes, e.g. *Streptomyces* bacteria, *Pseudonocardia* bacteria, *Nocardia* bacteria, *Rhodococcus* bacteria, *Mycobacterium* bacteria).

A vector may be any of integration vectors which are to be integrated into genome or autonomously replicating plasmids in the selected host. Preferred is a vector which can be stably maintained in the introduced cell, with the vdh gene supported thereon in a fit state for expression. In order to make the vdh gene express efficiently, an appropriate promoter functioning in the host may be used. Promoters can be classified into constitutive promoters and inducible promoters and it is recommended to select the one which exerts the most desirable effect in the production using the constructed transformed organisms. Specific promoters to be used includes promoters for bacteria such as lac promoter, trp promoter, tac promoter, T7 promoter, erm promoter, tip promoter and nit promoter; promoters for yeasts such as ADH promoter, PH05 promoter, gal10 promoter, PKG promoter and GAP promoter; promoters for animal cells such as SV40 early promoter; and promoter for plant cells such as 35S promoter of cauliflower mosaic virus.

It is necessary to use a vector suitable for the host cells to which the vector is introduced. Specific examples available for use include pBR322, pACYC184, pUC18, pKK223-2, pHSG398 (Takara Bio Inc.), pTrcHis (Invitrogen Corporation) and pET11a (Stratagene Corporation) in the case where *Escherichia coli* is used as a host; pBBR122 (Mobiotech) and pBHR1 (Mobiotech) for the other gram-negative bacteria; pHW1520 (Mobiotech) and pHY300PLK (Takara Bio Inc.) for *Bacillus*; pSH19 (Herai et al., Proc. Natl. Acad. Sci., 101, 14031-14035, 2004), pIJ702 (John Innes Centre), pIJ943 (John Innes Centre), pIJ8600 (John Innes Centre), pIJ602 (John Innes Centre), 1,pTip-vectors (Nakashima et al., Appli. Environ. Microbiol., 70, 5557-5568, 2004), pTYM19 (Onaka et al., J. Antibiot., 56, 950-956, 2003) for *actinomycetes*; and pAO815 (Invitrogen Corporation), pAUR101 (Takara Bio Inc.), pAUR123 (Takara Bio Inc.) and pAUR316 (Takara Bio Inc.) for fungi.

In order to make the vdh gene express using host-vector systems as mentioned above and to show hydroxylation activity, it is preferable to coexpress vdh and the gene coding Redox partner protein which is capable of transferring electrons efficiently to VDH (specifically, ferredoxin and ferredoxin reductase). The reason is because there is concern that, depending on the host, intrinsic Redox partner protein is not able to transfer electrons to VDH and therefore fails to show hydroxylation activity.

Examples of a gene coding Redox partner protein suitable for coexpression with the vdh gene includes those derived from the spinach as well as those derived from *Acinetobacter* sp. OC4 and *Rhodococcus erythropolis*. Preferred are thcCD gene (Nagy et al., J. Bacteriol. vol. 177, 676-687 (1995)) or homolog thereof which are a Redox partner derived from *Rhodococcus erythropolis* NI86/21 strain (NCAIM (P)B. 001020; National Collection of Agriculture and Industrial Microoraganisms (NCAIM, Budapest, Hungary).

The thcCD gene refers to thcC gene coding ferredoxin (ThcC) and thcD gene coding ferredoxin reductase (ThcD), and homolog thereof can be easily obtained by PCR using a pair of primer designed appropriately based on the gene information described in the above-mentioned documents and DNA isolated from *Rhodococcus* strain as a template. Use of such an expression system in which the gene coding Redox partner protein coexpresses enables an enhanced VDH activity to exhibit in various hosts without limitations depending on the compatibility of the intrinsic Redox partner protein of the host.

The culture of a transformed organism is performed in the medium which can be a nutritive medium of the transformed organism without affecting the transformation of the reaction substrate. Such a medium comprises an appropriate carbon source, nitrogen source, inorganic salt, natural organic nutrient and the like. As a carbon source, glucose, fructose, glycerol, sorbitol, organic acids can be used individually or in combination. The concentration of the carbon source is not particularly limited and preferably 1 to 10%. As a nitrogen source, ammonium, urea, ammonium sulfate, ammonium nitrate, ammonium acetate and the like can be used individually or in combination of two or more members thereof. As an inorganic salt, salts such as monopotassium phosphate, dipotassium phosphate, magnesium sulfate, manganese sulfate and ferrous sulfate can be used. In addition, as an organic nutrient source having growth-promoting effects of the bacteria to be used, peptone, meat extract, yeast extract, corn steep liquor and casamino acids can be used and furthermore, a small amount vitamins and nucleic acids may be contained in the medium.

In the production method of the present invention, when *Rhodococcus erythropolis* is used as a transformed organism, for example, the production method of the hydroxide of vitamin D or the like of the present invention can be provided by vitamin D or the like as a reaction substrate within the range of usual concentration of 0.1 to 10 mg/ml with the culture medium or the processed goods thereof obtained after cultivating the bacteria at a right temperature for the bacteria culture: e.g. at 10 to 35° C. in the medium suitable for the growth as mentioned above. The "processed goods" of the culture medium are the forms made by subjecting the culture medium to various treatments in order to performing the enzyme reaction efficiently and include a suspension of the bacterial cells, immobilized bacterium cells, crude VDH, purified VDH, immobilized VDH and modified VDH.

The transformed organisms obtained by introducing the vdh gene into the host as mentioned above has capability of accumulating hydroxide of vitamin D or the like more efficiently than ever before.

For example, the transformed organism obtained by introducing the vdh gene into *Rhodococcus erythropolis* of the present invention had properties to express abundant VDH and to grow faster compared to *Pseudonocardia autotrophica*, which is the original strain of the vdh gene. Also, the hydroxylation rate of vitamin $D_3$ was enhanced.

Furthermore, checking enzymological data of the VDH of the present invention, that is, Km value and $V_{max}$ value against vitamin $D_3$ and 25-hydroxy vitamin $D_3$ allows comparison of VDH and conventional hydroxylase which catalyzes the similar reactions. Km values of VDH for vitamin $D_3$ and 25-hydroxy vitamin $D_3$ determined by the method in Example 11 described below were 9.1 μM and 3.7 μM, respectively, and $V_{max}$ values were 243.9 mmol/min/mol of VDH and 588.2 mmol/min/mnol of VDH, respectively. Table 2 shows the results of the activity comparison of VDH and P450SU-1 (Sawada et al., Biochem. Biophys. Res. Commun., 320, 156-164, 2004), which is derived from bacteria and reported to have hydroxylation activity against vitamin $D_3$.

TABLE 2

|  | VDH | P450SU-1 | Human CYP27A1 | Mouse CYP27B1 |
|---|---|---|---|---|
| Km for $VD_3$ (μM) | 9.1 | 0.54 | 3.2 | N.D. |
| Vmax for $VD_3$ (mmol/min/mol of P450) | 243.9 | 16 | 270 | N.D. |
| Vmax/Km | 26.8 | 30 | 84 | N.D. |
| Km for 25-OH $VD_3$ (μM) | 3.7 | 0.91 | 3.5 | 0.05 |
| Vmax for 25-OH $VD_3$ (mmol/min/mol of P450) | 588.2 | 3.6 | 21 | 2730 |
| Vmax/Km | 159 | 3.9 | 6 | 54600 |

N.D.: Not determined

Regarding $V_{max}$ values, the VDH activity against vitamin $D_3$ and that against 25-hydroxy vitamin $D_3$ were about 15 times higher and about 163 times higher compared to those of P450SU-1, respectively. Also, VDH showed $V_{max}$ of hydroxylation activity at 25-position of vitamin $D_3$ equivalent to that of human CYP27A1, which is known to have hydroxylation activity at 25-position of vitamin $D_3$ (Sawada et al., Biochem. Biophys. Res. Commun., 320, 156-164, 2004). Furthermore, $V_{max}$ of VDH showed about one-fifth of the hydroxylation activity at 1α-position of mouse CYP27B1 (Uchida et al., Biochem. Biophys. Res. Commun., 320, 156-164, 2004) which is known to have hydroxylation activity at 1α-position of 25-hydroxy vitamin $D_3$. Accordingly, VDH was confirmed to have high hydroxylation activity in one enzyme at both of 25-position of vitamin $D_3$ and at 1α-position of 25-hydroxy vitamin $D_3$.

EXAMPLES

Hereinafter, the present invention is described in further detail in reference to examples and comparative examples, but should not be construed as being limited thereto.

Example 1

Preparation of the cell-free extract of *Pseudonocardia autotrophica* NBRC12473 strain After inoculating *Pseudonocardia autotrophica* NBRC12473 strain used for fermentative production of the hydroxide of vitamin $D_3$ (hereinafter referred to as "$VD_3$") in L-liquid medium (1.0% of Bacto-tryptone, 0.5% of yeast extract and 0.5% of sodium chloride) and cultivating at 30° C. for three days, cholesterol was then added thereto to a final concentration of 50 mg/ml and the strain was cultivated at 30° C. for another six hours. The obtained culture medium was subjected to centrifuged using a centrifuge, Beckman AVANTI J-E, at 6000 rpm for 15 minutes to harvest bacteria cells. The bacteria cells obtained from 3-liter of the culture fluid were suspended in 150 ml of buffer A (50 mM buffer fluid of potassium phosphate at pH 7.4, 10% of glycerol and 2 mM dithiothreitol). The cell suspension was subjected to cell disruption at 4° C. using 0.1 mm glass beads by a cell disruptor, Multi-beads shocker (manufactured by Yasui Kikai Corporation). In the cell disruption, ten cycles of one-minute shaking at 2500 rpm and one-minute stoppage were conducted. 110 ml of the cell-free extract obtained by centrifugation was dialyzed twice using 1 liter of buffer B (20 mM potassium phosphate at pH 7.4 and 20% glycerol). The precipitate was removed by centrifugation at 3000 rpm for 15 minutes so as to make the supernatant into a cell-free extract.

Example 2

Reconstitution of the Reaction System for Hydroxylation of $VD_3$ Using the Cell-Free Extract The following components were added to VDH partially-purified from the cell-free extract of *Pseudonocardia autotrophica* NBRC12743 strain by chromatographies using DEAE Sephacel column (Amersham Pharmacia Biotech Inc.) and Apative Macro-Prep Ceramic column (manufactured by BID-RAD Laboratories,; column-volume: 5 ml) was added to the reconstitution system composed of 160 mM sodium acetate, 32 ferredoxin derive from spinach (manufactured by Sigma-Aldrich Corp.), 0.1 U/ml ferredoxin reductase derived from spinach (manufactured by Sigma-Aldrich Corp.), 3 U/ml of glucose dehydrogenase, 2 mM of NADH, 2 mM of NADPH, 60 mM of glucose and 10 μM $VD_3$ in Buffer B. The resultant was subjected to reaction at 30° C. for 16 hours. Area values of 25-OH $VD_3$, 1α and 25-$(OH)_2VD_3$ were determined by HPLC anaysis and the area ratio of the hydroxide (25-OH $VD_3$, 1α and 25-$(OH)_2VD_3$) to the peak area attributed to all of the $VD_3$ compounds ($VD_3$, 25-OH $VD_3$, 1α and 25-$(OH)_2VD_3$) was calculated as a conversion rate.

Example 3

Purification of VDH

Dialyzed cell-free extract of *Pseudonocardia autotrophica* NBRC12473 strain was loaded onto a DEAE Sephacel column pre-equilibrated with Buffer B (Amersham Pharmacia Biotech Inc.; column volume: 20 ml). Bound proteins were eluted with a 200 ml linear gradient of 0 mM to 800 mM sodium acetate in Buffer B. The VDH activity in each fraction was measured and the fractions containing VDH the activity were collected. VDH was eluted at about 400 mM sodium acetate in DEAF Sephacel column chromatography. The collected fractions (55 ml) were dialyzed twice with 750 ml of Buffer C (7.5 mM sodium acetate buffer at pH 5.0 and 0.20% of glycerol). After the dialysis, precipitation was removed by centrifugation and the supernatant was loaded onto a CM Sepharose column pre-equilibrated with Buffer C (Amersham Pharmacia Biotech Inc.; column volume: 10 ml). The sample not absorbed by the column was subjected reprecipitation and the supernatant obtained by removing the precipitate by centrifugation was confirmed to have VDH activity. A sample (47 ml) sustaining the activity was dialyzed twice with one liter of Buffer D (2 mM potassium phosphate buffer at pH 7.4 and 20% of glycerol). The dialyzed sample was loaded onto an Apatite Macro-Prep Ceramic column pre-equilibrated with Buffer D (manufactured by BIO-RAD Laboratories, Inc.; column volume: 5 ml). Flow through fractions (75 ml) were loaded onto a Q Sepharose column (Amersham Pharmacia Biotech Inc.; column volume: 7 ml) pre-equilibrated with Buffer B. Bound proteins were eluted with a 100 ml linear gradient of 0 mM to 800 mM sodium acetate in Buffer B. The VDH activity in each fraction was measured and the fractions containing VDH were collected. VDH was eluted at about 550 mM sodium acetate in Q Sepharose column chromatography. The fractions containing VDH (22.5 ml) was concentrated to 2 ml by ultrafiltration using Amicon Ultra 30000 MWCO (manufactured by Millipore Corporation). The obtained sample was loaded onto a Sephacryl S-100 column (Amersham Pharmacia Biotech Inc.; column volume: 120 ml). The column chromatography was operated by AKTA system (Amersham Pharmacia Biotech Inc.). The VDH activity in each fraction was measured and pooled active fractions. The pooled sample (1.7 ml) was loaded onto a Mono-Q column (Amersham Pharmacia Biotech Inc.; column volume: 1 ml). The column chromatography was performed using AKTA system, and bound proteins were eluted with a 20 ml linear gradient of 0 mM to 800 mM sodium acetate in Buffer B (FIG. 3). The VDH activity in each fraction was measured and pooled active fractions. VDH was eluted at about 550 mM sodium acetate in Mono-Q column chromatography. The elution pattern of the proteins in each fraction was analyzed by sodium dodecyl sulfate (SDS)-polyacryl-amide gel electrophoresis (hereinafter called "SDS-PAGE") and the protein consistent with vitamin $D_3$ activity was identified as VDH (FIG. 3). In Mono-Q column chromatography two peaks having VDH activity and heme absorption were observed and a peak presumed attributable to VDH of about 45 kDa existed in both of the fractions.

Example 4

Determination of N-terminal Amino Acid Sequence and Internal Amino Acid Sequence of VDH 60 µl of sterilized water and 1200 µl of acetone were added to 180 µl of one of the samples (fraction 51) containing VDH protein and the resultant was cooled at −20° C. for 16 hours to thereby precipitate the protein in the sample. After removing supernatant by centrifugation at 13,000 rpm for 20 minutes, 20 µl of sample buffer of SDS-PAGE (62.5 mM sodium phosphate buffer at pH 7.0, 0.10% glycerol, 2% sodium dodecyl sulfate and 0.001% of bromophenol blue) was added to dissolve the protein. The sample was subjected to SDS-PAGE and the protein in the gel after the electrophoresis was transferred to a PVDF (polyvinylidene difluoride) membrane by a semi-dry blotter (manufactured by BIO-RAD Laboratories, Inc.; TRANS-BLOT SD SEMI-DRY TRANSFER CELL). The protein-absorbed on PVDF membrane was stained with a staining solution (0.1% Coomassie brilliant blue R-250, 10% acetic acid and 40% methanol) for two minutes and then destained by a destaining agent (10% acetic acid and 30% methanol) until the protein band can be confirmed. The PVDF membrane was air-dried, and then the VDH band was cut out and subjected to analysis of N-terminal amino acid sequence by Edman method using a high-sensitive amino acid sequence analyzer Procise 491 cLC (manufactured by Applied Biosystems Inc.). The obtained amino acid sequence is described by a single character code as follows:

```
                                    sequence ID No. 3
(N-terminal)-ALGTEQHDLFSGFFWQNPQPPYAA-
(C-terminal):
```

In order to determine the internal amino acid sequence of VDH, a VDH sample (fraction 46) precipitated by acetone was subjected to SDS-PAGE, stained with Coomassie brilliant blue R-250, and then destained by a destaining solution (25% methanol and 8% acetic acid) until the protein band can be confirmed. The VDH band was cut out and subjected to in-gel digestion with lysyl endopeptidase and to analysis by high performance liquid chromatography (HPLC) by conventional means, and then peptides were isolated by a high-sensitive amino acid sequence analyzer Procise 491 cLC (manufactured by Applied Biosystems Inc.). Among the four peptides obtained one sample was analyzed. The amino acid sequence obtained by the analysis is described by a single character code as follows:

```
                                    Sequence ID No. 4
(N-terminal)-LHGYLSDLLERK-(C-terminal):
```

Example 5

Preparation of Chromosomal DNA of *Pseudonocardia autotrophica* NBRC12473 Strain and *Rhodococcus erythropolis* NI86/21 Strain

*Pseudonocardia autotrophica* NBRC12473 strain was inoculated in L-liquid medium and cultivated at 30° C. for three days. The cultured cells were harvested by centrifugation at 3000 rpm for 10 minutes. Chromosomal DNA was isolated from the cells using the Isoplant DNA isolation kit (manufactured by Nippon Gene Co., Ltd.). In the same way chromosomal DNA of *Rhodococcus erythropolis* NI86/21 strain was prepared.

Example 6

Cloning of VDH Genes

In order to amplify the VDH gene by inverse PCR reaction, the following pair of primer were designed based on the N-terminal amino acid sequence obtained in Example 4:
VDH-I-1F: Sequence ID No. 5
VDH-I-1R: Sequence ID No. 6

In order to increase reactivity considering codon fluctuation, the following mixed nucleotides in equal quantities were used:
N: A+T+G+C, S: G+C, Y: C+T Next, a template for conducting the inverse PCR reaction was prepared by using a pair of primer (i.e. VDH-I-1F and VDH-I-1R). 4 µg of genome DNA of *Pseudonocardia autotrophica* NBRC12473 strain prepared in Example 5 was digested with a restriction enzyme, Aat II (manufactured by New England Biolads, Inc.), in 50 µl of a reaction solution at 37° C. for two hours. The digested DNA after the digestion was purified by the QIAquic PCR purification kit (manufactured by QIAGEN Genomics, Inc.) and eluted with 200 µl of the eluting buffer solution (containing 4 µg of DNA/200 µl). 50 µl of the solution was saved as a template of Linear DNA and an another 150 µl was added to T4 DNA Ligase (manufactured by New England Biolads, Inc.) and the provided buffer solution, thereby being subjected to self-ligation at 16° C. for 16 hours. The DNA was purified using the QIAquick PCR purification kit and eluted by 100 µl of 10 mM Tris HCl (at pH 8.5). The self-ligated sample was saved as a template of Circular DNA. Next, the inverse PCR reaction was performed with a pair of primer (VDH-I-1F and VDH-I-1R) using as templates the Linear DNA template and the Circular DNA template. The inverse PCR reaction was conducted using KOD plus polymerase (manufactured by TOYOBO Co., Ltd.) and the three-stage reaction comprising denaturation at 94° C. for one minute, annealing at 60° C. for 30 seconds and extension at 72° C. for three minutes was repeated 30 times in a PCR amplifier (GeneAmp PCR System 2700; manufactured by Applied Biosystems, Inc.). As a result, a DNA fragment in size about 1.2 kbp (hereinafter called "DNA fragment-A") was specifically amplified with the circular DNA as a template. After amplified DNA was separated by agarose gel electrophoresis, DNA fragment-A was cut off from the agarose gel and purified using QIAquick Gel extraction kit (manufactured by QIAGEN Genomics, Inc.). In order to analyze the nucleotide sequence of the DNA fragment-A, isolated DNA fragment-A was phosphorylated using T4 polynucleotide kinase (manufactured by New England Biolads, Inc.). Using the DNA Ligation kit ver. 2.1 (manufactured by Takara Shuzo Co., Ltd.), the phosphorylated DNA fragment-A was cloned into pBluescript II SK(+) (manufactured by TOYOBO Co., Ltd) which was in advance digested by EcoRV and dephosphorylated using calf intestine alkaline-phosphatase (manufactured by New England Biolads, Inc.). Ligated DNA was transformed into *Escherichia coli* XL1-Blue strain. Then, the transformants carrying plasmid inserted DNA fragment-A were selected on the L agar medium containing ampicillin (50 µg/ml), X-gal (5-bromo-4-chloro-3-indolyl-β-D-galactoside; 40 µg/ml) and Isopropyl-β-thiogalactopyranoside (IPTG; 100 µM). The positive colony of the *Escherichia coli* was cultivated in L liquid medium containing ampicillin (50 µg/ml) and the plasmid DNA was isolated and purified from cultured bacteria cells using the QIAprep Spin Miniprep kit (manufactured by QIAGEN Genomics, Inc.). The nucleotide sequence of 1201 bp DNA fragment-A integrated in the plasmid was determined using the DNA sequence analyzer ABI PRISM (registered trademark) 3100 Genetic Analyzer (manufactured by Applied Biosystems, Inc.). Furthermore, in order to obtain the full-length sequence of the VDH gene, the following pair of primer were newly designed based on the VDH coding region sequence in the DNA fragment-A and used for the inverse PCR reaction:

VDH-I-2F: Sequence ID No. 7
VDH-I-2R: Sequence ID No. 8

The inverse PCR reaction was conducted in the same way as in the above-mentioned method except that the *Pseudonocardia autotrophica* NBRC12473 strain was digested by Bam HI instead of Aat II. As a result, a DNA fragment in size about 1.2 (hereinafter called "DNA fragment-B") was specifically amplified with the Circular DNA as a template. The sequence of DNA fragment-B was determined using the same operation as for DNA fragment-A. As a result of the nucleotide sequence analysis, a nucleotide sequence of in size 1451 bp was confirmed. DNA fragment-B overlaps with DNA fragment-A (FIG. 4) and full length of the VDH gene was determined by assembling DNA fragment-A and DNA fragment-B.

Example 7

Construction of VDH Expression Vector pVDH-camAB

In order to construct a vector co-expressing camAB (ferredoxin reductase genes and ferredoxing genes) derived from *Pseudonocardia putida* strain and the vdh gene using *Escherichia coli* BL21(DE3) (Novagen) as a host, the VDH gene was amplified using the primers as follows:

VDH-1F: Sequence ID No. 9
VDH-1R: Sequence ID No. 10

The PCR reaction was conducted with a pair of primer (VDH-1F and VDF-1R) using genomic DNA of *Pseudonocardia autotrophica* NBRC12473 strain digested with Bgl II as a template. The inverse PCR reduction was conducted using Pfu turbo DNA polymerase (manufactured by TOYOBO Co., Ltd.) and the three-stage reaction comprising denaturation at 98° C. for 20 seconds, annealing at 63° C. for 30 seconds and extension at 72° C. for two minutes was repeated 25 times in a PCR amplifier. As a result, a DNA fragment in size about 1.2 kbp (hereinafter called "DNA fragment-C") was amplified. The DNA fragment-C was purified using QIAquick Gel extraction kit and digested with Nde I and Spe I. This DNA was separated by agarose gel electrophoresis and a DNA fragment in size 1.2 kbp was cut off from the agarose gel, and then purified using the QIAquick Gel extraction kit. The isolated DNA fragment-C was inserted into the Ndi I site and Spe I site of the vector pT7NS-camAB co-expressing ferredoxin reductase and ferredoxin derived from *Pseudomonas putida* (Arisawa et al., PCT Publication WO2003/087381) and transformed into *Escherichia coli* XL1-Blue strain (manufactured by STRATAGENE). Then, using L-broth agar medium (1.0% Bacto-tryptone, 0.5% yeast extract, 0.5% sodium chloride and 1.5% agar) containing ampicilline (50 µg/ml), the transformed *Escherichia coli* was selected. The colony of the thus-isolated *Escherichia coli* was cultivated in the L liquid medium. Plasmid DNA was isolated and purified from the bacteria cells of the proliferated transformed *Escherichia coli* using QIAprep Spin Miniprep kit to thereby obtain pVDH-camAB. The analysis of the DNA sequence of the obtained plasmid showed that there was no mutation of the VDH gene and the VDH gene was inserted in the designated site. *Escherichia coli* BL21 (DE3) was transformed into BL21 (DE3)/pVDH-camAB using the plasmid.

Example 8

Test of $VD_3$ Conversion Using *Escherichia coli* strain BL21 (DE3)/pVDH-camAB

The colony of the transformed *Escherichia coli* strain BL21(DE3)/pVDH-camAB obtained in Example 7 was inoculated to 10 ml of the L liquid medium containing ampicilline (50 µg/ml) and cultivated at 37° C. for 16 hours. 5 ml of the obtained culture fluid was transferred to 500 ml of MCG liquid medium (0.54% disodium hydrogenphosphate, 0.05% sodium chloride, 0.1% ammonium chloride, 1% casamino acid, 0.4% glucose, 0.02% magnesium chloride, 0.0015% calcium chloride and 100 µM iron sulfate) containing ampicilline (50 µg/ml) and cultivated with shaking at 37° C. for 2.5 hours. After adding 15 ml ethanol and 50 ml of 50% glycerol to the culture fluid, the bacteria were cultivated at 22° C. for 20 minutes and IPTG (final concentration: 100 µM) and 5-aminolevulinic acid (final concentration: 80 µg/ml) were added thereto. Next, the bacteria were cultivated at 22° C. for 20 hours and the bacteria cells were harvested by centrifugation. The harvested bacteria cells were resuspended with 25 ml of Buffer A to be 20-fold higher density than that of the culture fluid.

To confirm the expression of VDH, reduced-CO difference spectral analysis (Omura et al., J. Biol. Chem., 239, 2370-2378, 1964) was performed. First, the cell suspension obtained by the method previously described was subjected to cell disruption at 4° C. using 0.1 mm glass beads by a cell disruptor, Multi-beads shocker (manufactured by Yasui Kikai Corporation). In the cell disruption, ten cycles of 30-second shaking at 2500 rpm and a 30-second break were conducted. The cell-disrupted solution was centrifuged at 12000 rpm for 10 minutes to thereby obtain a cell-free extract. 700 µl of the cell-free extract was transferred into each of two test tubes with caps and carbon monoxide was purged into one of the tubes. Then, a small amount of sodium hydrosulfite was added to the cell-free extract in both of the tubes. Taking the absorption spectrum at from 400 nm to 500 nm of the sample without the purge of carbon monoxide as the baseline level, the absorption spectrum at from 400 to 500 nm of the sample purged with carbon monoxide was scanned using a spectrophotometer (U-3210 SpectrophotoMeter manufactured by HITACHI, Ltd.). As a result, a characteristic peak at 450 nm in cytochrome P450 was observed and estimated concentration of VDH is 113 nM per culture.

Using the cell suspension prepared by the method described above, a conversion test of $VD_3$ was conducted. To 200 μl of 20 times concentrated cell extract, 775 μl of Buffer B, 5.2 μl of 100 mM $VD_3$, 20 μl of 10% RMCD (Randomly substituted methyl-β-cyclodextrin; manufactured by Ensuiko Sugar Refining Co., Ltd.) were added and the conversion reaction was conducted at 30° C. for 16 hours. RMCD used for the conversion reaction of $VD_3$ is an additive used for the production of HVD. After the reaction, the solution was extracted twice with 1.5 ml and 0.75 ml of ethyl acetate, respectively, and the ethyl acetate phase was collected and dried using an evaporator. To the residue 150 μl of methanol was added and the hydroxide of $VD_3$ was detected by HPLC analysis.

HPLC Conditions:
column: J' sphere ODS-H80 (I.D. 4.6×75 mm) manufactured by YMC Co., Ltd.
mobile-phase: (A) water, (B) acetonitrile
The chromatography was performed with a gradient system of (A) and (B) in time programs as follows:

TABLE 3

| Time | Mobile phase (B %) |
|---|---|
| 0 min. → 12 min. | 50% → 100% |
| 12 min. → 25 min. | 100% → 100% |
| 25 min. → 26 min. | 100% → 50% |
| 26 min. → 30 min. | 50% → 50% |

Flow rate: 1.0 ml/min.
Wavelength: 275 nm
Column temperature: 40° C.

As a result of the HPLC analysis, the hydroxide of $VD_3$ was not observed, which appeared to be caused because the electron transfer to VDH from CamA (ferredoxin reductase) and CamB (ferredoxin) co-expressed with VDH did not happen. Accordingly, a cell-free extract of the *Escherichia coli* BL21 (DE3)/pVDH-camAB strain was prepared to conduct a conversion test of $VD_3$. 160 mM sodium acetate, 32 μg/ml ferredoxin derived from spinach, 0.1 U/ml of ferredoxin reductase derived from spinach, 3 U/ml of glucose dehydrogenase (manufactured by TOYOBO Co., Ltd.), 2 mM of NADH, 2 mM of NADPH, 60 mM of glucose and 10 μM of $VD_3$ were added to the cell-free extract of the *Escherichia coli* BL21 (DE3)/pVDH-camAB strain as an enzyme source to perform the conversion reaction in Buffer B. The conversion reaction was conducted at 30° C. for 16 hours. The solution after the reaction was extracted twice with 1.5 ml and 0.75 ml of ethyl acetate and the ethyl acetate phase was collected and dried using an evaporator. 150 μl of methanol was added to the residue and the hydroxide of $VD_3$ was detected by HPLC analysis. As a result of HPLC analysis, 25-hydroxyvitamin $D_3$ (hereinafter called HVD), 1α,25-dihydroxyvitamin $D_3$ (hereinafter called DHVD) and 1α,17,25-trihydroxyvitamin $D_3$ (hereinafter called THVD) were detected. This result showed that VDH from *Pseudonocardia autotrophica* NBRC12473 strain was the enzyme converting $VD_3$ to HVD, DHVD and THVD.

Example 9

Construction of a Histidine-Tagged VDH (hereinafter Called VDH-His) Expression Vector pET29-VDH For analyzing substrate specificity and kinetics of VDH, VDH was expressed as histidine-tagged protein and purified using an Ni-NTA column. First an expression vector was constructed. In order to amplify the VDH gene, the following primers are constructed:
VDH-1F: Sequence ID No. 9
VDH-2R: Sequence ID No. 11

Next, using a pair of primer (VDH-1F and VDH-2R), a PCR reaction was conducted using as a template the genomic DNA of *Pseudonocardia autotrophica* NBRC12473 strain digested in advance with Bgl II. The PCR reaction was conducted using Pfu turbo and the three-stage reaction comprising denaturation at 98° C. for 20 seconds, annealing at 63° C. for 30 seconds and extension at 72° C. for two minutes was repeated 25 times in a PCR amplifier. As a result, a DNA fragment in size about 1.2 kbp (hereinafter called "DNA fragment-D") was amplified. The fragment was purified using the QIAquick PCR purification kit and digested with Nde I and XhoI. This sample was separated by agarose gel electrophoresis, a DNA fragment in size 1.2 kbp was cut off from the agarose gel. Using the QIAquick gel extraction kit, the DNA fragment-D digested with Nde I and XhoI was purified. Next, using the DNA Ligation kit ver. 2.1, the DNA fragment-D was cloned into pET29b which was in advance digested with Nde I and XhoI and purified to thereby transform into the *Escherichia coli*. Subsequently, the transformed *Escherichia coli* was selected on the L-agar medium containing Kanamycin (20 μg/ml). The colony of the transformed *Escherichia coli* was cultivated in the L liquid medium containing Kanamycin (20 μg/ml). The plasmid DNA, pET29-VDH, was purified from the bacteria cells of the proliferated transformed *Escherichia coli*. The analysis of the DNA sequence of the pET29-VDH showed that there was no mutation of the VDH gene and the VDH gene was inserted in the designated site. pET29-VDH was transformed into *Escherichia coli* BL21 (DE3), yielding *Escherichia coli* strain BL21 (DE3)/pVDH-camAB.

Example 10

Purification of VDH-His

The colony of the transformed *Escherichia coli* strain BL21(DE3)/pET29-VDH was inoculated to 10 ml of the L liquid medium containing Kanamycin (20 μg/ml) and cultivated at 37° C. for 16 hours. 5 ml of the obtained culture fluid was transferred to 500 ml of MCG-broth medium containing Kanamycin (20 μg/ml) and cultivated with shaking at 37° C. for 2.5 hours. After adding 15 ml ethanol and 50 ml of 50% glycerol to the culture fluid, the bacteria were cultivated at 22° C. for 20 minutes and then IPTG (final concentration: 100 μM) and 5-aminolevulinic acid (final concentration: 80 μg/ml) were added. The bacteria were further cultivated at 22° C. for 20 hours and the cultured cells were harvested by centrifugation. The harvested bacteria cells were resuspended with 25 ml of Buffer A to be 20-fold higher density than that of culture fluid.

In order to confirm whether VDH expressed as a histigine-tagged protein is still functionally acive, reduced-CO difference spectral analysis was conducted. As a result, a characteristic peak at 450 nm was observed and estimated concentration of VDH-His is 163 nM per culture.

In order to purify VDH-His, 22 ml of the cell suspension of the transformed *Escherichia coli* BL21(DE3)/pET29-VDH (20 times concentrated than the culture fluid) was subjected to cell disruption at 4° C. using 0.1 mm glass beads by a cell disruptor, Multi-beads shocker (manufactured by Yasui Kikai Corporation). In the cell disruption, three cycles of 30-second shaking at 2500 rpm and a 30-second break were conducted. The cell-disrupted solution was centrifuged at 3000 rpm for 15 minutes to obtain a cell-free extract. 160 mm sodium acetate, 32 µg/ml ferredoxin derived from spinach, 0.1 U/ml of ferredoxin reductase derived from spinach, 3 U/ml of glucose dehydrogenase (manufactured by TOYOBO Co., Ltd.), 2 mM of NADH, 2 mM of NADPH, 60 mM of glucose and 10 µM of VD$_3$ were added to the cell-free extract as an enzyme source to perform the conversion reaction in Buffer B. As a result of HPLC analysis by the method previously described, the production of HVD, DHVD and THVD was confirmed (FIG. 6A).

The cell-free extract of the transformed *Escherichia coli* BL21(DE3)/pET29-VDH (16 ml) was dialyzed twice with 500 ml of buffer B. The precipitate during the dialysis was removed by centrifugation and the supernatant was loaded onto an Ni-NTA column equilibrated by Buffer B (manufactured by QIAGEN Genomics, Inc.; column volume: 2 ml). The bound proteins were eluted with a 100 ml of the linear gradient of 0 mM to 300 mM imidazole in Buffer B. The VDH-His fractions are collected (19 ml) and dialyzed three times with 500 ml of Buffer B to remove imidazole. Resulting from the reduced-CO difference spectral analysis, the purified VDH-His solution showed that concentration of the enzyme in the solution was 2590 nM. As a result of the VD$_3$ conversion test using the purified VDH-His enzyme conducted at 30° C. for three hours, the production of HVD, DHVD and THVD was confirmed (FIG. 6B). The purified enzyme was kept at −20° C. until use.

Example 11

Analysis of VDH Kinetics

Using the purified VDH-His enzyme prepared in Example 10, enzyme kinetics of the hydroxylation activity at 25-position to VD$_3$ and that at 1α position to HVD was analyzed. The reaction solution was prepared so as to have compositions of 259 pmol/ml of VDH-His, 96 µg/ml ferredoxin derive from spinach, 0.1 U/ml ferredoxin reductase derived from spinach, 320 mM of sodium acetate, 3 U/ml of glucose dehydrogenase, 60 mM of glucose, 2 mM of NADH and 2 mM of NADPH in 1 ml of Buffer B. At each of the substrate concentrations of 0.1 µM, 0.5 µM, 1 µM, 2 µM, 5 µM, 10 µM, 20 µM, 30 µM, 50 µM and 100 µM, the reaction was initiated by adding NADH and NADPH. The reaction was conducted at 180 rpm, 30° C. for ten minutes. By adding 1.5 ml of ethyl acetate, the reaction was terminated and the reaction solution was extracted, and then it was extracted by the addition of 1.5 ml of ethyl acetate. The obtained ethyl acetate phase was dried by an evaporator and the residue was dissolved with 100 µl of methanol. By the HPLC analysis under the same conditions described in Example 8, a calibration curve of the hydroxide was constructed to determine the quantity of the product. By the HPLC analysis of the prepared samples, the quantities of HVD and DHVD production were determined using a calibration curve. In the measurement of the hydroxylation activity at 25-position in the case where the substrate is VD$_3$, the production of DHVD as well as that of HVD was confirmed. The hydroxylation activity at 25-position was determined in terms of the total amount of the HVD and DHVD obtained per unit (one minute). Based on the obtained results, a correlation diagram of the substrate concentration in cases where the substrate is VD$_3$ or HVD and the activity (mmol/min/mol of VDH: the substrate amount (mmol) catalyzed by VDH in one minute) (FIG. 7). Furthermore, Lineweaver-Burk plot (reciprocal plot) diagram was made to determine the Km value and V$_{max}$ value of VDH to VD$_3$ and HVD (FIG. 8). The Km value and V$_{max}$ value of VDH to VD$_3$ were 9.1 µM and 243.9 mmol/min/mol of VDH and those to HVD were 3.7 µM and 588.2 mmol/min/mol of VDH.

Example 12

Construction of the VDH Expression Plasmid in *Rhodococcus erythropolis*

The fragment of the VDH gene (DNA fragment-C) digested with Nde I and Spe I prepared in Example 7 was cloned into the Nde I and Spe I sites of pTipQT2 (Nakashima et al., Appl. Environ. Microbiol. 5557-5568, 2004) using the DNA Ligation Kit ver. 2.1, yielding pTipQT-VDH plasmid in size about 9.4 kbp.

Example 13

Construction of pTipQT-VDH-thcCD Plasmid Co-Expressing the vdh Gene and thcCD Gene in *Rhodococcus erythropolis*

In order to clone the gene coding ferredoxin (ThcC) and ferredoxin reductase (ThcD) derived from *Rhodococcus erythropolis* strain NI86/21 (Nagy et al., J. Bacteriol. 676-687, 1995), the following primers (ThcCD-1F and ThcCD-1R) were designed:

ThcCD-1F: Sequence ID No. 12
ThcCD-1R: Sequence ID No. 13

Next, DNA was amplified by the PCR reaction using a pair of primer (TchCD-1F and ThcCD-1R) and the genome of *Rhodococcus erythropolis* NI86/21 prepared in Example 5 as a template. The PCR reaction was conducted using KOD plus polymerase and the three-stage reaction comprising denaturation at 98° C. for 20 seconds, annealing at 55° C. for 30 seconds and extension at 72° C. for two minutes was repeated 25 times in a PCR amplifier. As a result, a DNA fragment in size about 1.5 kbp (hereinafter called "DNA fragment-E") was amplified. The fragment was purified using the QIAquick PCR purification kit and digested with Hind III and BamH I. This sample was isolated by agarose gel electrophoresis, a DNA fragment in size 1.5 kbp was cut off from the agarose gel. Using the QIAquick gel extraction kit, the DNA fragment-E digested with Hind III and BamH I was purified. Next, using the DNA Ligation kit ver. 2.1, the DNA fragment-E was cloned into pUC (manufactured by TOYOBO Co., Ltd.) which was in advance digested with Hing III and BamH I, yielding pUC18-thcCD plasmid.

In order to remove the Nde I site existing in the gene coding ThcCD, the following two primers were designed to conduct the inverse PCR:

ThcCD IPCR-1F: Sequence ID No. 14
ThcCD IPCR-2R: Sequence ID No. 15

Using the two kinds of primers (ThcCD IPCR-1F and ThcCD IPCR-2R), inverse PCR was conducted. The inverse PCR was conducted using Pfu turbo polymerase and the three-stage reaction comprising denaturation at 94° C. for one minute, annealing at 50° C. for one minute and extension at 72° C. for seven minutes was repeated 25 times in a PCR amplifier. As a result, a DNA fragment in size about 4.3 kbp (hereinafter called "DNA fragment-F") was amplified. The reaction solution containing the DNA fragment-F amplified by the inverse PCR was separated by agarose gel electrophoresis. The DNA fragment in size 4.3 kbp was cut off from the agarose gel and recovered using the QIAquick gel extraction kit (manufactured by QIAGEN Genomics, Ltd.). Next, using the DNA Ligation kit ver. 2.1, the obtained DNA fragment-F was ligated to yield pUC18-thcCD-1. By the analysis of the DNA sequence, it was confirmed that the Ndi I site (CATATG) in the thcCD gene had been substituted with a non-recognition site (CATATG).

In order to clone the thcCD gene from pUC18-thcCD-1, the following primers are constructed:
ThcCD-2F: Sequence ID No. 16
ThcCD-1R: Sequence ID No. 13

Next, using a pair of primer (ThcCD-2F and ThcCD-1R), DNA was amplified by PCR using pUC18-thcCD-1 as a template. The PCR was performed using KOD plus polymerase and the three-stage reaction comprising denaturation at 98° C. for 20 seconds, annealing at 55° C. for 30 seconds and extension at 72° C. for two minutes was repeated 25 times in a PCR amplifier. As a result, a DNA fragment in size about 1.5 kbp (hereinafter called "DNA fragment-G") was amplified. The fragment was purified using the QIAquick PCR purification kit and digested with Nde I and BamH I. This sample was separated by agarose gel electrophoresis, a DNA fragment in size 1.5 kbp was cut off from the agarose gel. Using the QIAquick gel extraction kit, the DNA fragment-G digested with Nde I and BamH I was purified. Next, using the DNA Ligation kit ver. 2.1, the DNA fragment-G was cloned into pNitRC2 which was in advance digested with Nde I and BamH I, yielding pNitRC-thcCD plasmid.

In order to clone the ribosome binding site sequence from 5' upstream region of multiple cloning site in pNitRC2 and the thcCD gene sequence, the following primers are constructed:
ThcCD-3F: Sequence ID No. 17
ThcCD-2R: Sequence ID No. 18

Next, using a pair of primer (ThcCD-3F and ThcCD-2R), DNA was amplified by PCR using pNitRC-thcCD as a template. The PCR was performed using KOD plus polymerase and the three-stage reaction comprising denaturation at 98° C. for 20 seconds, annealing at 55° C. for 30 seconds and extension at 72° C. for two minutes was repeated 25 times in a PCR amplifier. As a result, a DNA fragment in size about 1.5 kbp (hereinafter called "DNA fragment-H") was amplified. The fragment was purified using the QIAquick PCR purification kit and digested with Xba I and EcoR I. This sample was separated by agarose gel electrophoresis, a DNA fragment in size 1.5 kbp was cut off from the agarose gel. Using the QIAquick gel extraction kit, the DNA fragment-H digested with Xba I and EcoR I was purified. Next, using the DNA Ligation kit ver. 2.1, the DNA fragment-H was cloned into pUC18 which was in advance digested with Xba I and EcoR I, yielding pUC18-RBS-thcCD plasmid.

To remove the Nde I site existing between the ribosome binding site and thcCD gene in pUC18-RBS-thcCD, the following primers were designed to conduct inverse PCR:
ThcCD-IPCR-2F: Sequence ID No. 19
ThcCD-IPCR-2R: Sequence ID No. 20

Using a pair of primer (ThcCD-IPCR-2F and ThcCD-IPCR-2R), inverse PCR was conducted using pUC18-RBS-thcCD as a template. The inverse PCR was performed using Pfu turbo polymerase and the three-stage reaction comprising denaturation at 94° C. for one minute, annealing at 50° C. for one minute and extension at 72° C. for seven minutes was repeated 25 times in a PCR amplifier. As a result, a DNA fragment in size about 4.3 kbp (hereinafter called "DNA fragment-I") was amplified. The reaction solution containing the DNA fragment-I amplified by the inverse PCR was separated by agarose gel electrophoresis. The DNA fragment in size 4.3 kbp was cut off from the agarose gel and recovered using the QIAquick Gel extraction kit. The obtained DNA fragment-I was phosphorylated with T4 polynucleotide kinase and subjected to self-ligation using the DNA Ligation Kit ver. 2.1 to obtain pUC18-RBS-thcCD-1. The analysis of the DNA sequence confirmed that the Nde I site (CATATG) had been substituted with a non-recognition site (CACATG).

In order to clone a gene coding ThcCD containing a ribosome binding site from pUC18-RBS-thcCD-1, the following primers were constructed:
ThcCD-4F: Sequence ID No. 21
ThcCD-3R: Sequence ID No. 22

Next, using a pair of primer (ThcCD-4F and ThcCD-3R), DNA was amplified by PCR using pUC18-RBS-thcCD-1 as a template. The PCR was performed using KOD plus polymerase and the three-stage reaction comprising denaturation at 98° C. for 20 seconds, annealing at 55° C. for 30 seconds and extension at 72° C. for two minutes was repeated 25 times in a PCR amplifier. As a result, a DNA fragment in size about 1.5 kbp (hereinafter called "DNA fragment-J") was amplified. The fragment was purified using the QIAquick PCR purification kit and digested with Spe I and Bgl II. This sample was separated by agarose gel electrophoresis, a DNA fragment in size 1.5 kbp was cut off from the agarose gel. Using the QIAquick gel extraction kit, the DNA fragment-J digested with Spe I and Bgl II was purified using QIAquick Gel extraction kit.

In order to construct the thiostrepton-inducible plasmid having cloning sites in the order of Nde I, Spe I and Bgl II sites, the following linkers were designed:
Linker NSBS-1: Sequence ID No. 23
Linker NSBS-2: Sequence ID No. 24

Linker NSBS-1 and Linker NSBS-2 were mixed so that each reached a final concentration of 5 pmol/μl, heated at 98° C. and cooled to 30° C. over a period of 30 minutes. The linkers were introduced into pTipQT2 digested with Nde I and Sal I (Nakashima et al., Appl. Envrion. Microbiol. 5557-5568, 2004) using DNA Ligation Kit ver. 2.1 to obtain pTipQT-NSBS.

The above-mentioned DNA fragment-J digested with Spe I and Bgl II was cloned into pTipQT-NSBS using DNA Ligation Kit ver. 2.1 to thereby obtain pTipQT-NS-thcCD.

The fragment of the VDH gene digested with Nde I and Spe I prepared in Example 7 (DNA fragment-C) was linked to the Nde I and Spe I sites of pTipQT-NS-thcCD using DNA Ligation Kit ver. 2.1 to construct pTipQT-VDH-thcCD in size about 10.9 kbp (FIG. 9).

Example 14

Transformation of *Rhodococcus erythropolis* JCM 3201 Strain by pTipQT2, pTipQT-VDH and pTipQT-VDH-thcCD

*Rhodococcus erythropolis* JCM 3201 strain was cultivated in 100 ml of the L liquid medium at 30° C. with shaking until it enters the logarithmic phase. The culture liquid was cooled with ice for 30 minutes and centrifuged to recover bacteria cells. After cells were resuspended with 100 ml of ice-cold water, the suspension was centrifuged to recover bacteria cells. After cells were resuspended with 100 ml of ice-cold 10% glycerol solution, the suspension was centrifuged to recover bacteria cells. After another repetition of this washing with iced 10% glycerol solution, the bacteria cells were resuspended with 5 ml of ice-cold 10% glycerol solution. Each 400 μl of the suspension was snap frozen in liquid nitrogen and stored at −80° C. until use. The bacteria cells taken out from the storage at −80° C. was thawed on ice and mixed with 3 μl of pTipQT2, pTipQT-VDH or pTipQT-VDH-thcCD plasmid (about 300 ng each) was added. The mixed solution of the bacteria cells and DNA was transferred to electroporation cuvette (0.2 cm gap cuvette; manufactured by Bio-Rad Laboratories, Inc.) and electric pulses with an electric intensity of 12.5 kV/cm were applied to each sample using the electroporation system of Bio-Rad Laboratories, Inc., Gene Pulser II, by setting the pulse controller to the capacitance of 25 μF and external resistance of 400 Ω. The electric pulse-treated solution of the bacteria cells and DNA was mixed with 1 ml of the L-broth agar medium (agar concentration: 1.5%) and cultured at 30° C. for two hours. The cultured bacteria were spread onto L-agar plate containing 20 μg/ml tetracycline (agar concentration: 1.5%) and cultured at 30° C. for three days to thereby obtain the transformant of each plasmid.

Example 15

$VD_3$ Conversion Test by the Transformant of *Rhodococcus erythropolis*

The transformant of *Rhodococcus erythropolis* JCM 3201 strain produced in Example 14 was cultivated in 20 ml of L liquid medium containing 8 μg/ml of tetracycline at 30° C. When the cell density reached 0.8 OD at a wavelength of 600 nm (OD 600), thiostrepton (solvent: dimethylsulfoxide) was added to a final concentration of 1 μg/ml to express VDH, ThcC and ThcD. After 24-hour culture, cells were harvested by centrifugation. 4 ml of Buffer A was added and a cell suspension (five times concentrated than the culture fluid) was obtained. Using the prepared cell suspension of the transformant, $VD_3$ conversion test was conducted. 767 μl of Buffer B, 13 μl of 100 mM $VD_3$, and 20 μl of 10% randomly substituted methyl-β-cyclodextrin (RMCD) were added to 200 μl of the cell suspension of the transformant and subjected to reaction at 30° C. for 18 hours. RMCD used in the $VD_3$ conversion test is an additive used for the production of HVD. After the reaction, the suspension was extracted twice with 1.5 ml and 0.5 ml of ethyl acetate, respectively, and the ethyl acetate phase was collected and dried with an evaporator. 150 μl of methanol was added to the residue and subjected to HPLC analysis to detect the hydroxide of $VD_3$ (FIG. 10). As a result of the conversion, the production of HVD was confirmed in the strain expressing VDH and the concentration of HVD was determined. A cell-free extract was prepared from the cell suspension of the transformant and subjected to the reduced-CO difference spectroscopy to determine the expression amount of VDH. As a result, the expression amount of VDH per culture fluid was of the strains transformed by pTipQT2, pTipQT-VDH and pTipQT-VDH-thcCD were 0, 1747 and 1256 nM, respectively. When adjusting hydroxide-generating relative activity using the expression amount of VDH, the strains transformed by pTipQT-VDH and by pTipQT-VDH-thcCD had the relative activity per expressed VDH of 20.2 and 119.2 mmol/min/mol of VDH, respectively. The results showed that the relative activity of the transformant co-expressing VDH and ThcCD was nearly six-fold higher than that of the transformant expressing VDH solely (Table 4).

TABLE 4

| Transformant | Expression amount of VDH (nM) | Activity (mmol/min/mol of VDH) |
| --- | --- | --- |
| pTipQT2 | N.D. | — |
| pTipQT-VDH | 1747 | 20.2 |
| pTipQT-VDH-thcCD | 1256 | 119.2 |

Example 16

Construction of Plasmid pVDH-thcCD Co-Expressing VDH and ThcCD in *Escherichia coli*

In order to amplify a DNA fragment containing the vdh gene and thcCD gene, the following primers were constructed:
VDH-1F: Sequence ID No. 9
ThcCD-3R: Sequence ID No. 22

Next, DNA was amplified by the PCR reaction using a pair of primer (VDH-1F and ThcCD-3R) and pTipQT-VDH-thcCD prepared in Example 15 as a template. The PCR reaction was conducted using KOD plus polymerase and the three-stage reaction comprising denaturation at 98° C. for 20 seconds, annealing at 55° C. for 30 seconds and extension at 72° C. for three minutes was repeated 25 times in a PCR amplifier. As a result, a DNA fragment in size about 3.0 kbp (hereinafter called "DNA fragment-K") was amplified. The fragment was purified using the QIAquick PCR purification kit and digested with Nde I and Bgl II. This sample was separated by agarose gel electrophoresis, a DNA fragment in size about 3.0 kbp was cut off from the agarose gel. Using the QIAquick gel extraction kit, the DNA fragment-K digested with Nde I and Bgl II was purified. Next, using the DNA Ligation kit ver. 2.1, the DNA fragment-E was joined to pET29b which was in advance digested with Nde I and Bgl II to thereby obtain pVDH-thcCD plasmid. *Escherichia coli* BL21(DE3) was transformed by the plasmid to thereby obtain BL21(DE3)/pVDH-thcCD *Escherichia coli* strain.

Example 17

$VD_3$ Conversion Test Using BL(DE3)/pVDH-thcCD *Escherichia coli* Strain

The colony of *Escherichia coli* strain BL21(DE3)/pVDH-thcCD was inoculated with 2 ml L liquid medium containing Kanamycin (20 μg/ml) and cultivated at 37° C. for 16 hours. 250 μl of the obtained culture fluid was transferred to 250 ml of L liquid medium containing Kanamycin (20 μg/ml) and cultivated with shaking at 37° C. for 2.5 hours. After adding 750 μl ethanol and 2.5 ml of 50% glycerol to the culture fluid, the bacteria were cultivated at 22° C. for 20 minutes and then IPTG (final concentration: 100 μM) and 5-aminolevulinic acid (final concentration: 80 μg/ml) were added. The bacteria were further cultivated at 22° C. for 20 hours and then the bacteria cells were harvested by centrifugation. The harvested bacteria cells were resuspended with 5 ml of Buffer A to obtain a cell suspension of *Escherichia coli* BL21(DE3)/pVDH-thcCD (five times concentrated than the culture fluid).

To confirm the expression of VDH, reduced-CO difference spectral analysis (Omura et al., J. Biol. Chem., 239, 2370-2378, 1964) was conducted. First, the cell suspension of transformed *Escherichia coli* BL21(DE3)/pVDH-thcCD obtained by the method previously described was subjected to cell disruption at 4° C. using 0.1 mm glass beads by a cell disruptor, Multi-beads shocker (manufactured by Yasui Kikai Corporation). In the cell disruption, ten cycles of 30-second shaking at 2500 rpm and a 30-second break were conducted. The cell-disrupted solution was centrifuged at 12000 rpm for 10 minutes to thereby obtain a cell-free extract. 700 μl of the cell-free extract was transferred into each of two test tubes with caps and one of the tubes was purged with carbon monoxide. Then, a small amount of sodium hydrosulfite was added to the cell-free extract in both of the tubes. Taking the absorption spectrum at from 400 nm to 500 nm of the sample without the purge of carbon monoxide as the baseline level, the absorption spectrum at from 400 nm to 500 nm of the sample purged with carbon monoxide was scanned using a spectrophotometer (U-3210 SpectrophotoMeter manufactured by HITACHI, Ltd.). As a result, a characteristic peak at 450 nm in cytochrome P450 was observed, which showed VDH expression of 258 nM per culture fluid.

Using the cell suspension of *Escherichia coli* BL21(DE3)/pVDH-thcCD prepared by the method described above, a conversion test of $VD_3$ was conducted. To 200 μl of the cell suspension of *Escherichia coli* BL21(DE)/pVDH-thcCD (five times concentrated cell extract), 767 μl of Buffer B, 13 μl of 200 mM $VD_3$, 20 μl of 10% RMCD (randomly substituted methyl-β-cyclodextrin) were added and the conversion reaction was conducted at 30° C. for 19 hours. As a control group, cultured cells of the host BL21(DE3) strain cultivated under the same conditions as those for *Escherichia coli* BL21(DE3)/pVDH-thcCD. RMCD used for the conversion reaction of $VD_3$ is an additive used for the production of HVD. The cell suspension after the reaction was extracted twice with 1.5 ml and 0.75 ml of ethyl acetate, and the ethyl acetate phase was collected and dried using an evaporator. To the residue 150 μl of methanol was added, thereby detecting the hydroxide of $VD_3$ by HPLC analysis (in the same way as in Example 8).

As a result of the HPLC analysis, the generation of HVD was observed (FIG. 11). The result showed that the co-expression of the vdh gene and thcCD gene enabled the hydroxylation of $VD_3$ using *Escherichia coli* as a host.

Example 18

Hydroxylation Test of Vitamin $D_2$ ($VD_2$) and 7-Dehydrocholesterol Using VDH

Using the purified VDH-His enzyme prepared in Example 10, conversion of $VD_2$ and 7-dehydrocholesterol was conducted. A reaction solution was prepared so as to be made into the composition of 259 pmol/ml of VDH-His, 32 μg/ml ferredoxin derive from spinach (manufactured by Sigma), 0.1 U/ml ferredoxin reductase derived from spinach (manufactured by Sigma), 3 U/ml of glucose dehydrogenase, 60 mM of glucose, 20 μM of substrate ($VD_2$, 25-OH $VD_2$ and 7-dehydrocholesterol), 2 mM of NADH and 2 mM of NADPH in 1 ml of Buffer B. 0.004% RMCD was added only to the solution for converting 7-dehydrocholesterol. The reaction was initiated by the addition of NADH and NADPH and incubated at 30° C. and 180 rpm for 60 minutes for the conversion of $VD_2$ and 90 minutes for the conversion of 7-dehydrocholesterol. By adding 1.5 ml of ethyl acetate, the reaction was terminated and the reaction solution was extracted, and it was again extracted by the addition of 0.75 ml of ethyl acetate. The obtained ethyl acetate phase was dried by an evaporator and the residue was dissolved by 100 μl of methanol. The dissolved solution was subjected to HPLC analysis for the detection of the hydroxide of $VD_2$ and 7-dehydrocholesterol.

HPLC Conditions (for $VD_2$):
column: J' sphere ODS-H80 (I.D. 4.6×75 mm) manufactured by YMC
mobile-phase: (A) water, (B) acetonitrile
The chromatography was performed with a gradient system of (A) and (B) in time programs as follows:

TABLE 5

| Time | Mobile phase (B %) |
|---|---|
| 0 min. → 10 min. | 53% → 53% |
| 10 min. → 14 min. | 53% → 100% |
| 14 min. → 21 min. | 100% → 100% |
| 21 min. → 23 min. | 100% → 53% |
| 23 min. → 30 min. | 53% → 53% |

Flow rate: 1.0 ml/min.
Wavelength: 265 nm
Column temperature: 40° C.
HPLC conditions (for 7-dehydrocholesterol):
column: J' sphere ODS-H80 (I.D. 4.6×75 mm) manufactured by YMC Co., Ltd.
mobile-phase: (A) water, (B) acetonitrile
The chromatography was performed with a gradient system of (A) and (B) in time programs as follows:

TABLE 6

| Time | Mobile phase (B %) |
|---|---|
| 0 min. → 6 min. | 50% → 100% |
| 6 min. → 23 min. | 100% → 100% |
| 23 min. → 24 min. | 100% → 50% |
| 24 min. → 28 min. | 50% → 50% |

Flow rate: 1.0 ml/min.
Wavelength: 240 nm
Column temperature: 40° C.

The result of the HPLC analysis showed that the VDH converted from $VD_2$ as a substrate to 25-OH $VD_2$. It also showed that the conversion from 25-OH $VD_2$ as a substrate to 25,28-$(OH)_2VD_2$ and 25,26-$(OH)_2VD_2$. Furthermore, the conversion of 25-OH-7-dehydrocholesterol from 7-dehydrocholesterol was confirmed by using VDH. These results show that VDH is capable of producing the hydroxide of various steroids.

Example 19

Acquisition of a Homolog of the vdh Gene

In order to amplify the vdh gene or homologs thereof, the following primers were constructed:
VDH-101F: Sequence ID No. 25
VDH-106R: Sequence ID No. 26

Next, DNA was amplified by PCR using these two primers and the genomic DNA prepared from *Pseudonocardia autotrophica* in the same way as in Example 5 as a template. The PCR was conducted using LA Taq polymerase (manufactured by Takara Bio Inc.) and the three-stage reaction comprising denaturation at 95° C. for five minutes, annealing at 52° C. for 30 seconds and extension at 72° C. for two minutes was repeated 30 times in a PCR amplifier. After the amplification reaction, 4 μl of the reacted solution was separated by electrophoresis using 0.8% agarose gel. As a result, a DNA fragment in size about 1.2 kbp was amplified in all of the tested strains. The 38 strains tested are shown in the following list. In this list, "*Pseudonocardia*" is abbreviated as "P.".

TABLE 7

| Strains |
|---|
| *P. autotrophica* DSM535 |
| *P. autotrophica* DSM43082 |
| *P. autotrophica* DSM43083 |
| *P. autotrophica* DSM43084 |
| *P. autotrophica* DSM43085 |
| *P. autotrophica* DSM43086 |
| *P. autotrophica* DSM43087 |
| *P. autotrophica* DSM43088 |
| *P. autotrophica* DSM43090 |
| *P. autotrophica* DSM43091 |
| *P. autotrophica* DSM43093 |
| *P. autotrophica* DSM43094 |
| *P. autotrophica* DSM43095 |
| *P. autotrophica* DSM43096 |

TABLE 7-continued

Strains

P. autotrophica DSM43097
P. autotrophica DSM43098
P. autotrophica DSM43099
P. autotrophica DSM43100
P. autotrophica DSM43101
P. autotrophica DSM43102
P. autotrophica DSM43103
P. autotrophica DSM43104
P. autotrophica DSM43105
P. autotrophica DSM43106
P. autotrophica DSM43107
P. autotrophica DSM43108
P. autotrophica DSM43128
P. autotrophica DSM43129
P. autotrophica DSM43558
P. autotrophica ATCC13181
P. autotrophica ATCC19727
P. autotrophica ATCC33795
P. autotrophica ATCC33796
P. autotrophica ATCC33797
P. autotrophica JCM4010
P. saturnea IFO14499
P. saturnea FERM BP2307
P. autotrophica 4M1067

BRIEF DESCRIPTION OF DRAWINGS

[FIG. 1] A schematic drawing of the hydroxylation reaction of vitamin $D_3$ by Pseudonocardia autotrophica NBRC12743 strain

[FIG. 2] Effect of the sodium acetate concentration on the activity of the vitamin D hydroxylase

[FIG. 3] A graph indicating the elution pattern of Mono-Q chromatography shown as the change of absorbance for the fraction number

[FIG. 4] An SDS-PAGE image of the purified VDH

[FIG. 5] A view showing the cloning of a gene coding VDH

[FIG. 6] A chart showing the HPLC analysis result of the conversion test of vitamin $D_3$ using a cell-free extract of the VDH-His expression strain (FIG. 6A) and purified VDH-His (FIG. 6B)

[FIG. 7] A graph showing the correlation of the substrate concentration and the VDH activity

[FIG. 8] A graph showing the Lineweaver-Burk plot (reciprocal plot) of the vitamin $D_3$ hydroxylation activity at 25-position and 25-OH vitamin $D_3$ hydroxylation activity at 1α-position

[FIG. 9] A view showing the construction of VDH expression plasmids pTipQT-VDH and pTipQT-VDH-thcCD

[FIG. 10] A chart showing the HPLC analysis result of the conversion test of vitamin $D_3$ by the transformed Rhodococcus erythropolis (pTipQT2 in FIG. 10a, pTipQT-VDH in FIG. 10b and pTipQT-VDH-thcCD in FIG. 10c)

[FIG. 11] A chart showing the HPLC analysis result of the conversion test of vitamin $D_3$ by Escherichia coli BL21(DE3) strain (FIG. 11a) and Escherichia coli BL21(DE3)/pVDH-thcCD strain (FIG. 11b)

[FIG. 12] A chart showing the HPLC analysis result of the conversion test of vitamin $D_2$ and 25-OH vitamin $D_2$ by VDH ("a" is a chart of the control experiment)

[FIG. 13] A chart showing the HPLC analysis result of the conversion test of 7-dehydrocholesterol by VDH ("a" is a chart of the control experiment)

---

The invention claimed is:

1. An isolated polynucleotide encoding a hydroxylase selected from (a)-(c):
   (a) an isolated polynucleotide comprising nucleotides 320-1531 of SEQ ID NO: 1; and
   (b) an isolated polynucleotide that hybridizes under stringent conditions to a polynucleotide entirely complementary to nucleotides 320-1531 of SEQ ID NO: 1, wherein said hybridization under stringent conditions is hybridization at 65° C. in the presence of 0.7-1.0M sodium chloride; and
   (c) an isolated polynucleotide comprising a polynucleotide sequence having at least 90% nucleic acid sequence identity to nucleotides 320-1531 of SEQ ID NO: 1.

2. An isolated host cell transformed with the polynucleotide of claim 1.

3. The host cell of claim 2, wherein said host cell is *Escherichia coli* or an actinomycete.

4. A method for producing a hydroxide of a vitamin D compound or 7-dehydrocholesterol, comprising:
   (a) culturing the cell of claim 2 in a culture medium under conditions in which the polypeptide encoded by said polynucleotide is expressed; and
   (b) contacting a vitamin D compound or 7-dehydrocholesterol with said culture medium, or with a purified extract of said culture medium containing said polypeptide, whereby a hydroxide of said vitamin D compound or 7-dehydrocholesterol is produced.

5. The method of claim 4, wherein said cell further expresses redox partner proteins during said culturing.

6. The method of claim 4, wherein the hydroxide of the vitamin D compound is 1α, 25-dihydroxy vitamin $D_3$.

7. The method of claim 4, wherein the hydroxide of the vitamin D compound is 25-dihydroxy vitamin $D_3$.

8. The method of claim 4, wherein the hydroxide of the vitamin D compound is 25-dihydroxy vitamin $D_2$.

9. An isolated polynucleotide selected from (a) and (b):
   (a) an isolated polynucleotide comprising a polynucleotide sequence encoding the amino acid sequence of SEQ ID NO: 2; and
   (b) an isolated polynucleotide that hybridizes under stringent conditions to a polynucleotide entirely complementary to a polynucleotide encoding the amino acid sequence of SEQ ID NO: 2, wherein said hybridization under stringent conditions is hybridization at 65° C. in the presence of 0.7-1.0M sodium chloride, wherein the polynucleotide encodes a hydroxylase.

* * * * *